(12) United States Patent
Huang et al.

(10) Patent No.: US 7,952,349 B2
(45) Date of Patent: *May 31, 2011

(54) APPARATUS AND METHOD UTILIZING MAGNETIC FIELD

(75) Inventors: Jiankang Huang, Roslindale, MA (US); Hariharan Venketesh Sundram, Brookline, MA (US); Robert C. O'Handley, Andover, MA (US); David C. Bono, Wellesley, MA (US)

(73) Assignee: Ferro Solutions, Inc., Woburn, MA (US)

( * ) Notice: Subject to any disclaimer, the term of this patent is extended or adjusted under 35 U.S.C. 154(b) by 1036 days.

This patent is subject to a terminal disclaimer.

(21) Appl. No.: 11/734,181

(22) Filed: Apr. 11, 2007

(65) Prior Publication Data

US 2007/0282378 A1 Dec. 6, 2007

Related U.S. Application Data

(63) Continuation-in-part of application No. 11/652,272, filed on Jan. 11, 2007, and a continuation-in-part of application No. 10/730,355, filed on Dec. 8, 2003, now abandoned.

(60) Provisional application No. 60/791,004, filed on Apr. 11, 2006, provisional application No. 60/758,042, filed on Jan. 11, 2006, provisional application No. 60/790,921, filed on Apr. 11, 2006, provisional application No. 60/431,487, filed on Dec. 9, 2002.

(51) Int. Cl.
*G01R 33/02* (2006.01)
*G01R 29/22* (2006.01)

(52) U.S. Cl. ........................................ 324/249; 324/109

(58) Field of Classification Search .................. 324/109, 324/151 R, 244, 249, 260; 365/157; 73/779, 73/861.08, 861.77, 862.69
See application file for complete search history.

(56) References Cited

U.S. PATENT DOCUMENTS

| | | |
|---|---|---|
| 4,823,617 A | 4/1989 | Hase et al. |
| 5,658,485 A | 8/1997 | Cava et al. |
| 5,675,252 A | 10/1997 | Podney |
| 5,940,362 A | 8/1999 | Plonsky et al. |
| 6,437,558 B2 | 8/2002 | Li et al. |
| 6,515,382 B1 | 2/2003 | Ullakko |
| 6,580,271 B2 | 6/2003 | Li et al. |
| 6,610,427 B2 | 8/2003 | Kashiwaya et al. |
| 6,686,205 B1 | 2/2004 | Schultz et al. |

(Continued)

FOREIGN PATENT DOCUMENTS

JP 11258077 A 9/1999

OTHER PUBLICATIONS

International Search Report and Written Opinion in International Application No. PCT/US07/066463 mailed Sep. 28, 2007.

(Continued)

*Primary Examiner* — Bot L LeDynh
(74) *Attorney, Agent, or Firm* — Rissman Hendricks & Oliverio LLP

(57) ABSTRACT

Apparatus and method for harvesting energy from the environment and/or other external sources and converting it to useful electrical energy. The harvester does not contain a permanent magnet or other local field source but instead relies on the earth's magnetic field of another source of a magnetic field that is external to the sensing device. One advantage of these new harvesters is that they can be made smaller and lighter than energy harvesters that contain a magnet and/or an inertial mass.

15 Claims, 10 Drawing Sheets

U.S. PATENT DOCUMENTS

| | | |
|---|---|---|
| 6,279,406 B1 | 8/2004 | Li et al. |
| 6,809,515 B1 | 10/2004 | Li et al. |
| 6,809,516 B1 | 10/2004 | Li et al. |
| 6,835,463 B2 | 12/2004 | Srinivasan |
| 6,984,902 B1 | 1/2006 | Huang et al. |
| 7,023,206 B2 | 4/2006 | Viehland et al. |
| 2001/0028245 A1 | 10/2001 | Li et al. |
| 2002/0011123 A1 | 1/2002 | O'Boyle |
| 2002/0036282 A1 | 3/2002 | Chiang et al. |
| 2002/0172060 A1 | 11/2002 | Takeuchi |
| 2003/0197970 A1 | 10/2003 | Srinivasan |

OTHER PUBLICATIONS

Beeby et al., "Review Article" Measurement Science and Technology, Dec. 1, 2006, vol. 17, No. 12, Institute of Physics Publishing, Bristol, GB.

Amirtharaja, R., et al., "Self-Powered Signal Processing Using Vibration-Based Power Generation", IEEE Journal of Solid State Circuits, v. 33, n. 5, pp. 687-695 (1998).

Churchill, D.L., et al., "Strain Energy Harvesting for Wireless Sensor Networks," Smart Structures and Materials 2003: Smart Electronics, MEMS, BioMEMS, and Nanotechnology, Proceedings of SPIE, vol. 5055, (2003).

El-Hani, M., et al., "Design and Fabrication of a New Vibration-Based Electromechanical Power Generator", Sensors and Actuators, Elsevier Science B.V., 2001, pp. 335-342.

Ghandi, K., "Compact Piezoelectric Based Power generation", Continuum Controls, Inc., DARPA Energy Harvesting Program Review, 2000.

Glynne-Jones, P., et al., "An Electromagnetic, Vibration-Powered Generator for Intelligent Sensor Systems", Sensors and Actuators, pp. 344-349, Elsevier B.V.

Glynne-Jones, P., et al., "The Modelling of a Piezoelectric Vibration Powered Generator for Microsystems", Transducer '01—Eurosensors XV, The 11th International Conference on Solid-State Sensors and Actuators, Munich, Germany, Jun. 10-14, 2001, pp. 46-49.

Glynne-Jones, P., et al., "Towards a Piezoelectric Vibration-Powered Microgenerator", IEE Proc.-Sci Meas. Technol., vol. 148, No. 2, Mar. 2001, pp. 68-72.

Grimes, C.A., et al., "Magnetoelastic Sensors For Remote Query Environmental Monitoring" Smart Mater. Struct. 8 (1999( pp. 639-646, 1999 IOP Publishing Ltd., Printed in UK.

James, E.P., et al., "A Wireless Self-Powered Micro-System for Condition Monitoring", Department of Electronics and Computer Science, University of Southampton, Hampshire, England, 4 pages.

James, E.P., et al., "An Investigation of Self-Powered Systems for Condition Monitoring Applications", Sensors and Actuators, pp. 171-176, Elsevier B. V.

Li, Yi-Qun, et al., "An Innovative Passive Solid-State Magnetic Sensor", www.sensorsmag.com, Oct. 2000, pp. 52-54.

Lynch, B.J. et al., "A New Magnetic Sensor Technology", A New Magnetic Sensor Technology, pp. 13-20, presented in part at the Undersea Defence Technology Conference in London from Feb. 7-9, 1990.

Meninger, S., et al., "Vibration-to-Electric Energy Conversion", IEEE Transactions on VLSI Systems, v. 9, n. 1, p. 64 (2001).

Mermelstein, M.D., "Magnetoelastic Amorphous Metal Fluxgate Magnetometer", Electronics Letters, 1986, vol. 22, No. 10, pp. 525-526.

Mermelstein, M.D., et al., "Low-Frequency Magnetic Field Detection With a Magnetostrictive Amorphous Metal Ribbon", Applied Physics Letter 51, Aug. 1987, pp. 545-547.

Mermelstein, Marc D., "A Magnetoelastic Metallic Glass Low-Frequency Magnetometer", IEEE Transactions on Magnetics, vol. 28, No. 1, Jan. 1992, p. 36-56.

Mori, Kiyotaka, et al., "Magnetoelectric Coupling in Terfenol-D/Polyvinylidenedifluoride Composites", Applied Physics Letters, vol. 81, No. 1, Jul. 1, 2002, pp. 100-101.

Pantinakis, A., et al., "High-Sensitivity Low-Frequency Magnetometer Using Mangetostrictive Primary Sensing and Piezoelectric Signal Recovery", Electronics Letters, 1986, vol. 22, No. 14, pp. 737-738.

Prieto, J. L., et al., "Magnetization Processes and Optimal Performance of Magnetostrictive Piezoelectric Sensors", Journal of Applied Physics, vol. 79, No. 9, May 1, 1996, pp. 7099-7105.

Roundy, Shad, et al., "A Study of Low Level Vibrations as a Power Source for Wireless Sensor Nodes", Computer Sommunications 26 (2003) pp. 1131-1144, Elsevier Science B.V.

Ryu, Jungho, et al., "Magnetoelectric Properties in Piezoelectric and Magnetostrictive Laminate Composites", Japanese Journal of Applied Physics, vol. 40, Part 1, No. 8, pp. 4948-4951, Aug. 2001.

Shearwood, C., et al., "Development of an Electromagnetic Microgenerator", Electronics Letters.

Shenck, N.S., et al., "Energy Scavenging with Shoe-Mounted Piezoelectrics", IEEE Microelectronics, v. 21, n. 3, May-Jun. 2001, p. 30-42.

Shin, K.H., et al., "Preparation and Properties of Elastically Coupled Electro-Magnetic Elements With a Bonding Structure", IEEE Transactions on Magnetics, vol. 34, No. 4, Jul. 1998, pp. 1324-1326.

Van Suchtelen, J., "Product Properties: A New Application of Composite Materials", Philips Res. Repts. 27, pp. 28-37, 1972.

White N.M., et al., "A Novel Thick-Film Piezoelectric Micro-Generator", Smart Materials and Structures 10, 2001, p. 850-852, Institute of Physics Publishing.

White, N.M., et al., "Design and Modelling of a Vibration-Powered Micro-Generator", Measurement + Control, vol. 34, Nov. 2001, pp. 267-271.

Williams, C.B., et al., "Analysis of a Micro-Electric Generator For Microsystems," Transducer '95—Eurosensors IX, The 8th International Conference on Solid-State Sensors and Actuators, and Eurosensors IX, Stockholm, Sweden, Jun. 25-29, 1995, pp. 369-372.

Van Den Boomgaard, et al. "Magnetoelectricity In Piezoelectric-Magnetostrictive Composites",Ferroelectrics, 1976, vol. 10, pp. 295-298.

Van Den Boomgaard, et al., "Piezoelectric-Piezomagnetic Composites With Magnetoelectric Effect", Ferroelectrics, 1976, vol. 14, pp. 727-728.

Levitin, R.Z., et al., "Magnetostriction measurements under high magnetic fields by a piezoelectric transducer glued on the sample", Physica B 177 (1992) 59-62.

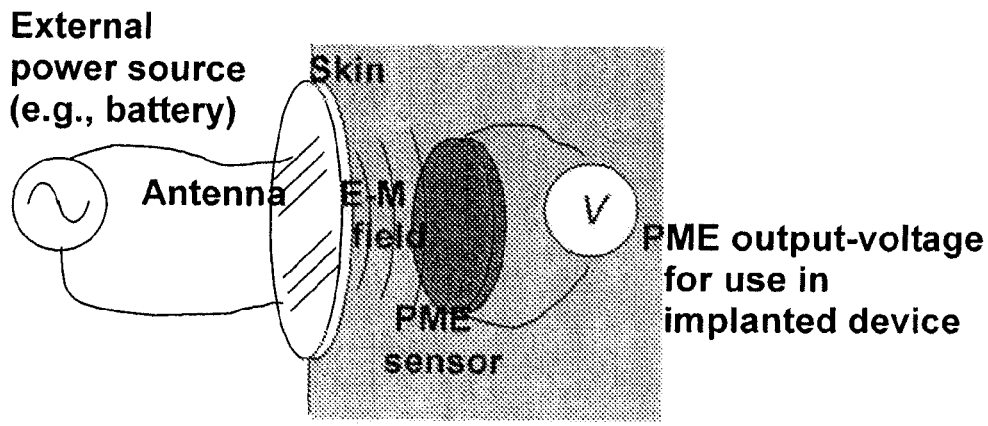

Fig. 11. Schematic of the invented system of wireless power transmission for implanted devices. External power source energizes flat "patch" coil antenna that emits magnetic-rich electromagnetic wave. Implanted passive magnetostrictive/electro-active (PME) sensor/transducer receives and converts the AC magnetic field to AC voltage that is processed to produce the power needed for the particular application.

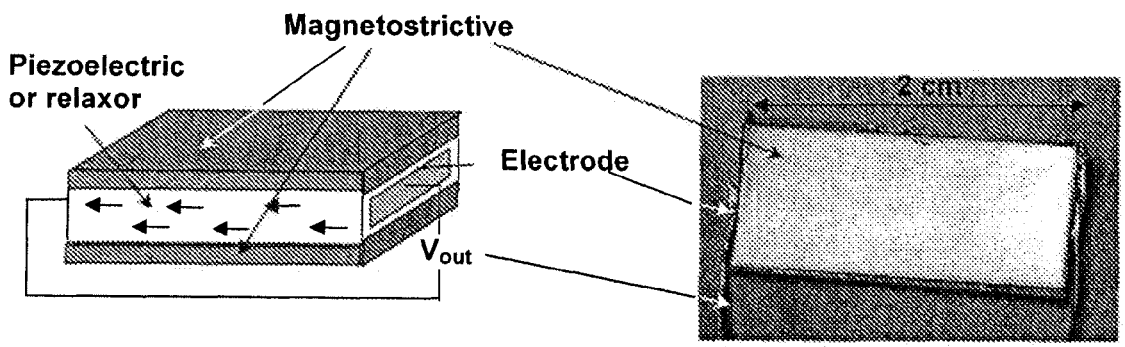

Fig. 12. Schematic of the PME-33 showing poled electro-active element with magnetostrictive outer layers bonded to the electro-active component and end electrodes providing for $g_{33}$ operation. Photo at right is of prototype PME-33 made by Ferro Solutions.

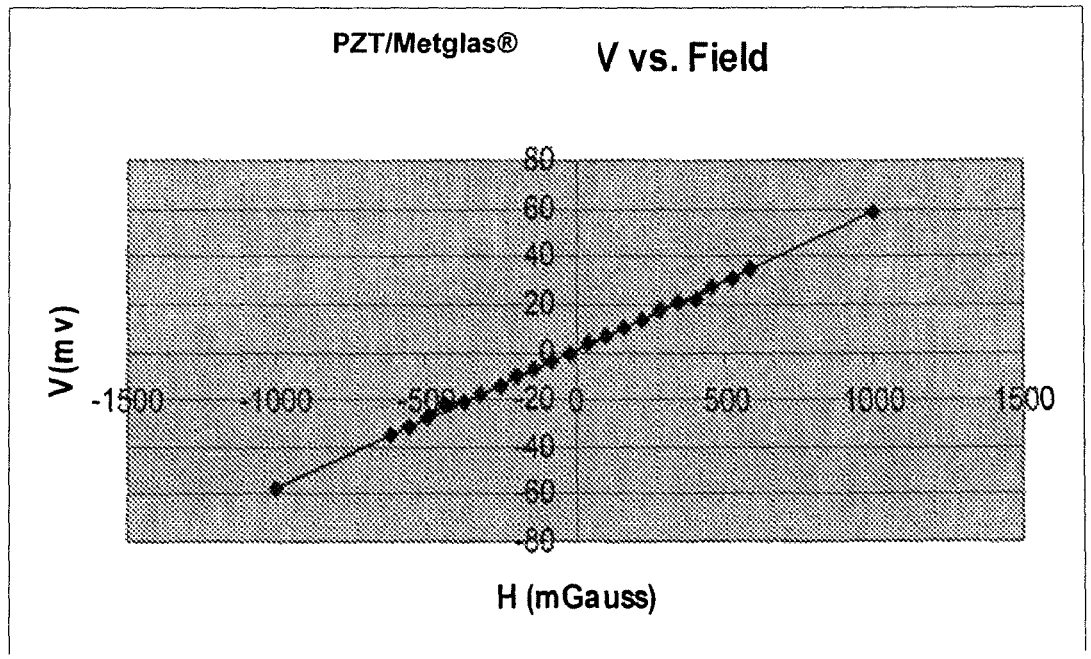
Fig. 13. Sensor voltage output (mV) vs. magnetic field (mOe) in an early (2002) Ferro Solutions prototype PME-33 sensor with a sensitivity of 0.06 V/Oe.
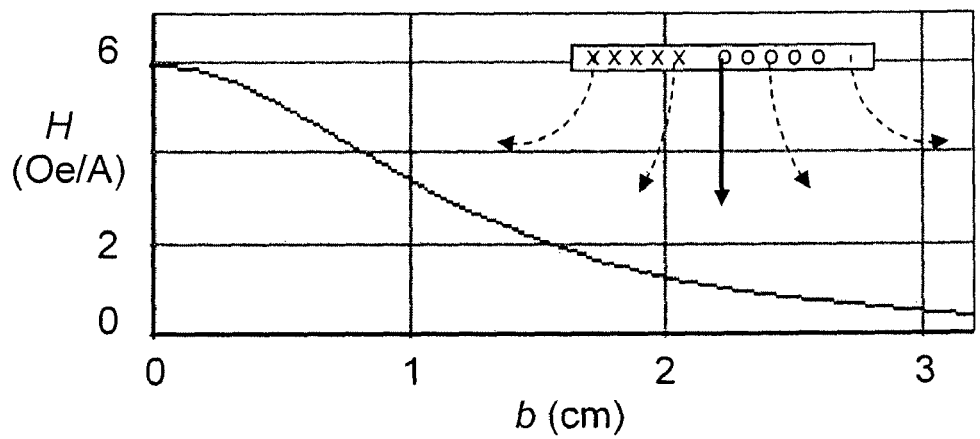
Fig. 14 Plot of Eq. 3 showing decrease in field-per-Ampere with distance $b$ along the normal to the coil.

APPARATUS AND METHOD UTILIZING MAGNETIC FIELD

RELATED APPLICATIONS

This application claims the benefit of priority to U.S. Provisional Application No. 60/791,004, filed Apr. 11, 2006, and is a continuation-in-part of U.S. application Ser. No. 11/652,272, filed Jan. 11, 2007, which claims the benefit of priority to U.S. Provisional Application No. 60/758,042, filed Jan. 11, 2006, and U.S. Provisional Application No. 60/790,921, filed Apr. 11, 2006, and is a continuation-in-part of U.S. application Ser. No. 10/730,355, filed Dec. 8, 2003, which claims the benefit of priority to U.S. Provisional Application No. 60/431,487, filed Dec. 9, 2002, the disclosures of which are incorporated herein by reference in their entirety.

FIELD OF THE INVENTION

This invention relates to apparatus and methods for harvesting energy from the environment and other sources external to the harvester and converting it to useful electrical energy. The present invention generally relates to implantable stimulator systems and methods, and more particularly relates to implantable stimulator systems and methods utilizing one or more implantable microstimulators for direct electrical current. Specifically outlined is the use of PME for the delivery of microstimulation through applied external magnetic field technology. The delivered therapy will be effective for continuous or temporary, as needed (PRN) therapeutic intervention.

BACKGROUND OF THE INVENTION

Energy harvesters are known that convert vibrational energy into electrical energy. The electrical energy produced can then be stored or used by other devices. For example, the vibrations of an air conditioning duct can be converted into electrical energy by an energy harvester and the electrical energy then used to power a sensor that measures the air temperature in the duct. The sensor does not require electrical wiring to a remote source of power or periodic battery changes.

There are a variety of such devices for generating electrical power from vibrations, oscillations or other mechanical motions. Generally such devices are categorized as inductive, capacitive, and/or piezoelectric devices. While each of the known types of vibrational energy harvesters have different advantages, they also have drawbacks such as: the need for heavy, powerful permanent magnets (in the case of inductive energy harvesters) to produce a sufficiently large flux density; an auxiliary source of power, such as a battery (in the case of capacitive harvesters); the need for large vibration frequencies and/or a heavy inertial mass to generate sufficient vibrational energy for harvesting (for all types of vibration energy harvesters); undesirable levels of damping and noise generation from interaction between the locally generated magnetic field and nearby metallic parts (for inductive harvesters); and other disadvantages such as size or weight that make them unsuitable for use in a remote or generally inaccessible location.

As shown in FIG. 1, a typical magnetic device 2 to harvest vibrational energy consists of a permanent magnet 3 (an internal local field source) attached to a housing 7 and connected by a spring 4 to a passive magnetic field sensor 5 (e.g., an induction coil or a passive magnetostrictive/electroactive field sensor). External vibrations cause a relative motion of the magnet 3 and sensor 5, producing an electrical voltage across a load 8 and a current through the load. In addition to requiring a local magnetic field source (e.g., a permanent magnet disposed adjacent to the field sensor), these devices also typically include an inertial mass 6 (also known as a proof mass) to increase the vibrational energy generated. The inertial mass may be rigidly attached to the sensor (as shown), may be the same or separate from the permanent magnet, or may comprise part of the sensor itself. As a further alternative, the magnet may comprise part of the moving proof mass, as opposed to being fixed to the housing. In each case, the inertial mass and the permanent magnet increase the size and weight of the device.

It would be desirable to provide a magnetic energy harvester that does not require a local magnetic field source as part of the device itself. It would also be beneficial to provide a magnetic energy harvester that does not require a source of vibrational or other mechanical motion.

SUMMARY OF THE INVENTION

In accordance with various embodiments of the present invention, an apparatus is provided for harvesting energy from the environment or other remote sources and converting it to useful electrical energy. The harvester does not contain a permanent magnet or other local field source but instead relies on the earth's magnetic field or another source of a magnetic field that is external to the sensing device. One advantage of these new harvesters is that they can be made smaller and lighter than energy harvesters that contain a magnet. Another advantage is that they do not require vibrational energy to function.

According to various embodiments of the invention disclosed herein, the harvester differs from those of the prior art by the absence of a permanent magnet or other local (internal) field source. In these new devices, a change in the state of magnetization of the sensing element may be achieved in one (or both) of two general ways:

1. The magnetic flux density in the sensing element may be altered by changes in the orientation of the sensor (movement of the sensor) with respect to a static (non-changing) external field. For example, the magnetization vector M of the sensing element may rotate due to changes in the orientation of the sensing element with respect to the earth's field. Such movement of the sensing element may be achieved by attaching the sensing element to a piece of rotating machinery or a rotating part on a vehicle. Alternatively, the sensing element may be suspended on its axis and allowed to rotate (due to external vibrations), the rotation causing a change in its orientation in the earth's field.
2. Alternatively, the sensing element may remain stationary and be operated on by a remote changing magnetic field from any of a variety of sources. The remote changing magnetic field can be produced by an electrical transformer, motor, electronic device, moving machinery or inductive wire or coil which is relatively remote (acting at a distance or through a non-magnetic barrier) on the sensing element. The changing (e.g., alternating) magnetic field source can be designed to couple with a remote sensing element efficiently in terms of frequency, distance, field orientation and magnitude to deliver power remotely to the sensing element.

When operating from the earth's magnetic field, the power harvested may be less than that achieved with a prior art vibrational energy harvester having a built-in magnetic field.

The power harvested from a remote field source will be measured in microwatts per centimeter cubed ($\mu$W/cm$^3$), as opposed to milliwatts per centimeter cubed (mW/cm$^3$) for energy harvesters that include a strong magnet. However, for certain applications the power delivered by such a small, lightweight and simple energy harvester will be sufficient and enable new applications.

When operating near some man-made external sources of alternating magnetic fields, or when such an external field source is brought near to the energy harvester, the power harvested can be considerably greater because the strength of such fields is often considerably greater than the earth's magnetic field ($H_{earth}$ is approximately 0.3 Oe or 3 micro-Tesla).

A preferred sensing element for use in the present invention is based on a class of passive magnetostrictive electroactive (PME) magnetic field sensors that produce a voltage when exposed to a changing magnetic field. The sensing element is preferably a layered structure (e.g., sandwich) of magnetostrictive material bonded to an electroactive material, the latter being poled in a direction preferably parallel to the plane of the magnetostrictive layer(s). An external magnetic field causes a magnetization change in the magnetostrictive layer(s), which respond(s) with a magnetoelastic stress. Part of the stress is transferred to the electroactive layer that responds by producing a voltage given by $V_i=g_{ij}\sigma_j L_i$. Here, $L_i$ is the distance between the electrodes across which the voltage $V_i$ is measured, $\sigma_j$ is the stress transferred to the electroactive component, and $g_{ij}$ is the stress-voltage coupling coefficient. The voltage is greatest when the direction i=j. However, in different applications the principal stress and induced voltage may lie in orthogonal directions (e.g., 1-3 operation), or the principal stress and voltage may act along different axes (e.g., 1-5 operation).

The energy harvester of the present invention is more than a simple passive magnetostrictive/electroactive (PME) field sensor. A simple PME field sensor is comprised of materials and dimensions designed preferably to produce a large voltage across a high impedance circuit, the voltage being indicative of the field of interest. The electronic circuit for a simple PME sensor is designed to register a field value. In contrast, the PME energy harvester of the present invention is comprised of materials and dimensions designed preferably to produce a voltage and current that match the impedance of the load to be driven. The PME energy harvester is coupled to an electronic circuit that converts the PME output to power for immediate use or storage. The PME element is preferably optimized to respond to the field strength of the intended environment, which would generally be much greater than that of a pure field sensor.

This new type of energy harvester can be simpler, lighter and/or more compact than those requiring a permanent magnet as a field source, and also those requiring an inertial mass for enhancing vibrational energy. For example, suitable applications may include wireless monitoring applications, wherein wireless monitoring is meant to include self powered sensing of local conditions and processing of the sensor output and self powered wireless communication to a central data processing point. Other suitable applications might include wireless transfer of electrical power over a small distance to a location inaccessible via electrical leads or not convenient for battery replacement. More specifically, these applications may include supplying power for:

wireless health monitoring or condition based maintenance;

supplementing power or recharging batteries without physically accessing them;

elimination of wiring of electrical devices remote from a power source;

wireless monitoring of temperature, airflow, humidity and gas content in heating, ventilation and air conditioning (HVAC) systems;

wireless monitoring of traffic flow, turbulence, noise or personnel movement;

wireless, self powered security systems;

powering of mobile electronic instruments;

passive detection of creep or crack propagation in structures for condition based maintenance; and powering of devices implanted in a living body (or to another inaccessible location) for purposes of sensing, transmitting, or actuating (e.g., motors, pumps, switches, valves, electrodes), as well as for accomplishing therapy or other functions that require a voltage and/or current.

Furthermore, applications of the new energy harvester are not limited to vibration rich environments. A simple repetitive motion or rotation of the more sensitive PME devices as described herein allows them to operate from the earth's magnetic field. They can be placed in physically inaccessible locations and activated from a remote field source that is either present in the environment or placed there for the purpose of energizing the device.

In one embodiment of the invention: an energy harvester without a local field source comprises:

a magnetic field sensing element including one or more layers of magnetostrictive material having a magnetization vector that responds to variations in an applied magnetic field by generating a stress, and one or more layers of electroactive material, mechanically bonded to the layer of magnetostrictive material, that responds to the stress by generating a voltage; and a circuit coupled to the sensing element that converts the voltage to electrical power for immediate use or storage, wherein the sensing element either:

a) moves relative to a remote static external magnetic field, such that changes in orientation of the sensing element with respect to the external field generates the voltage; or b) is stationary with respect to a remote changing external magnetic field, wherein the changing external field causes the sensing element to generate the voltage.

In Various Embodiments the electrical power comprises a voltage and current suitable for an intended application;

the magnetostrictive material layer has a magnetization vector that responds to variations in the magnetic field by rotating in a plane and wherein the electroactive material is poled in a direction substantially parallel to the plane in which the magnetization vector rotates;

the sensing element is mounted to an object that moves relative to the applied magnetic field;

the variations in the applied external field are in one or more of magnitude and direction of the field;

the sensing element is mounted such that local vibration changes its orientation with respect to the applied magnetic field;

the sensing element includes electrodes for measuring the voltage generated and wherein the electrodes are configured such that the distance between the electrodes and cross sectional area between the electrodes are tailored to produce a desired electrical power;

the magnetization vector rotates relative to the electrode axis due to changes in the orientation of the sensor in the applied external field;

local vibrations also change the orientation of the sensor with respect to the applied external field;

the remote magnetic field is generated by one or more of an electrical transformer, motor, actuator, switch, electronic device, moving machinery or inductor;

the inductor is a wire or coil through which an alternating current is flowing, to produce the remote changing external magnetic field;

the sensing element is rigidly attached to an inertial mass;

the sensing element includes an inertial mass;

the changing external field or sensing element movement is at vibration or power transmission frequencies of no greater than 1 kHz;

the changing external field is at a resonance frequency in the range of that of the sensing element;

the changing external field is in a range of 20 to 50 kHz;

the external field frequency is equal to or close to the resonance frequency of the sensor, which varies roughly according to the equation $$fr \approx \frac{1}{2L}\sqrt{\frac{E_{eff}}{\rho_{eff}}}$$

where L is a characteristic length of the sensor and $E_{eff}$ and $\rho_{eff}$ are the elastic modulus and mass density appropriate to describe the composite magnetostrictive/electroactive sensor properties;

the changing external field and sensing element are within a resonant frequency range;

the circuit is within the resonant frequency range;

the external changing field is outside a human or other animal body and the sensing element is inside the body.

In another embodiment of the invention, a method of harvesting energy comprises:

providing a magnetic field sensing element including one or more layers of magnetostrictive material having a magnetization vector that responds to variations in an applied magnetic field by generating a stress, and one or more layers of an electroactive material, mechanically bonded to the layer of magnetostrictive material, that responds to the stress by generating a voltage;

wherein the voltage is generated by either:
  moving the sensing element relative to a remote static external magnetic field, such that changes in orientation in the sensing element with respect to the external field generates the voltage; or
  the sensing element is stationary with respect to a remote changing external magnetic field, and the changing external field causes the sensing elemenet to generate the voltage; and
  converting the generated voltage to electrical power for immediate use or storage.

The invention disclosed and claimed herein addresses the above and other needs and provides means and systems for acutely stimulating a nerve root(s), spinal nerve(s), organs, soft tissue, incision site or similar, with a miniature implantable neurostimulator(s) that can be implanted via a minimal surgical procedure and powered by an external magnetic field.

This invention describes a means of delivering power wirelessly from outside the body to inside the body for the therapies described above. The means of wireless power delivery consists of a passive magnetostrictive/electro-active (PME) magnetic-field sensor as the main component of a small implantable device that will receive a changing magnetic field from an external alternating magnetic field source external to the body. This field source may be a hand-held device or a small antenna affixed to the wearer's skin, clothing or accessories. Alternatively, the external field may be generated by a source planted in a chair, desk, car seat or table that the recipient frequents. The AC magnetic field excites the implanted PME sensor, which generates a voltage and current that can be used to provide therapeutic relief by stimulating nerve.

The therapeutic system can also be used to minimize tissue damage, reduce tumor size and burden, or stimulate bone or cartilage growth in the appropriate space. An AC magnetic field is a more efficient means of transmitting power than an AC electric field because of the greater attenuation of electric fields by body fluids.

The proposed system would include an external source of alternating magnetic field close to the recipient or in a wearable device that is made up of a power source (line power, battery, rechargeable battery or energy harvester) and electronics to control the signal generated by the wearable antenna. The antenna is connected to the wearable device with a wire and affixed to the skin or cloth in the area of interest to perform two functions: First, the antenna transmits data to communicate with the implanted devices. Second, the antenna transmits a signal that is converted by the implanted PME sensor/harvester (part of the implanted device) into useful power for the entire implanted device.

The implanted PME provides a tiny implant that may be millimeter scale in size that can be driven by an external magnetic field applied only on an as needed basis. For example, patients with migraine headaches can be treated with therapeutic electricity applied to the occipital nerve. The patient does not however express this headache chronically, rather the headache appears only on an intermittently acute basis. Therefore applying the magnetic field during the earliest (prodromal) period of the headache can prevent conversion to a migraine headache. This would be one therapeutic embodiment of the technology.

Stimulation and control parameters of the implanted micro-stimulator are preferably adjusted to levels that are safe and efficacious with minimal patient discomfort. Different stimulation parameters generally have different effects on neural tissue, and parameters are thus chosen to target specific neural populations and to exclude others. For example, large diameter nerve fibers (e.g., A-.alpha. and/or A-.beta. fibers) respond to relatively lower current density stimulation compared with small diameter nerve fibers (e.g., A-.delta. and/or C fibers). Stimulation patterns for non neural therapy (tumor beds and incision sites) are delivered at the range of therapeutic efficacy.

The microstimulator used with the present invention preferably possesses one or more of the following properties: at least one PME for applying stimulating current to surrounding tissue and acting as a sensor for determination of therapeutic efficacy and time constants related to the flow of current; electronic and/or mechanical components encapsulated in a hermetic package made from biocompatible material(s); a coil that generates an AC magnetic field to deliver energy and/or information to the implanted PME wirelessly; a means for receiving and/or transmitting signals via telemetry; means for receiving and/or storing electrical power within the microstimulator; and a form factor making the microstimulator implantable via a minimal surgical procedure.

A microstimulator may operate independently, or in a coordinated manner with other implanted devices, or with external devices. In addition, a microstimulator may incorporate means for sensing pain, which it may then use to control stimulation parameters in a closed loop manner. According to one embodiment of the invention, the sensing and stimulating means are incorporated into a single microstimulator. According to another embodiment of the invention, a sensing means communicates sensed information to at least one microstimulator with stimulating means.

Thus, the present invention provides a therapy for chronic pain that utilizes one or more miniature PME's as neurostimulators and is minimally invasive. The simple implant procedure results in minimal surgical time and possible error, with associated advantages over known treatments in terms of reduced expense, reduced operating time, single implant surgery, and therapy provided on an as needed basis. Other advantages, inter alia, of the present invention include the system's monitoring and programming capabilities, the power source, storage, and transfer mechanisms, the activation of the device by the patient or clinician, the system's open and closed-loop capabilities and closed-loop capabilities coupled with sensing a need for and/or response to treatment, coordinated use of one or more stimulators, and the small size of the stimulator.

These and other advantages of the present invention may be better understood by referring to the following detailed description and accompanying drawings.

BRIEF DESCRIPTION OF THE DRAWINGS

FIG. 11 is a schematic of the invented system of wireless power transmission for implanted devices; external power source energizes flat "patch" coil antenna that emits magnetic-rich electromagnetic wave; implanted passive magnetostrictive/electro-active (PME) sensor/transducer receives and converts the AC magnetic field to AC voltage that is processed to produce the power needed for the particular application;

FIG. 12 is a schematic of the PME-33 showing poled electro-active element with magnetostrictive outer layers bonded to the electro-active component and end electrodes providing for $g_{33}$ operation; photo at right is of prototype PME-33 made by Ferro Solutions;

FIG. 13 is a graph showing sensor voltage output (mV) vs. magnetic field (mOe) in an early (2002) Ferro Solutions prototype PME-33 sensor with a sensitivity of 0.06 V/Oe; and FIG. 14 is a plot of Eq. 3 showing decrease in field-per-Ampére with distance b along the normal to the coil.

DETAILED DESCRIPTION

Figure 1:
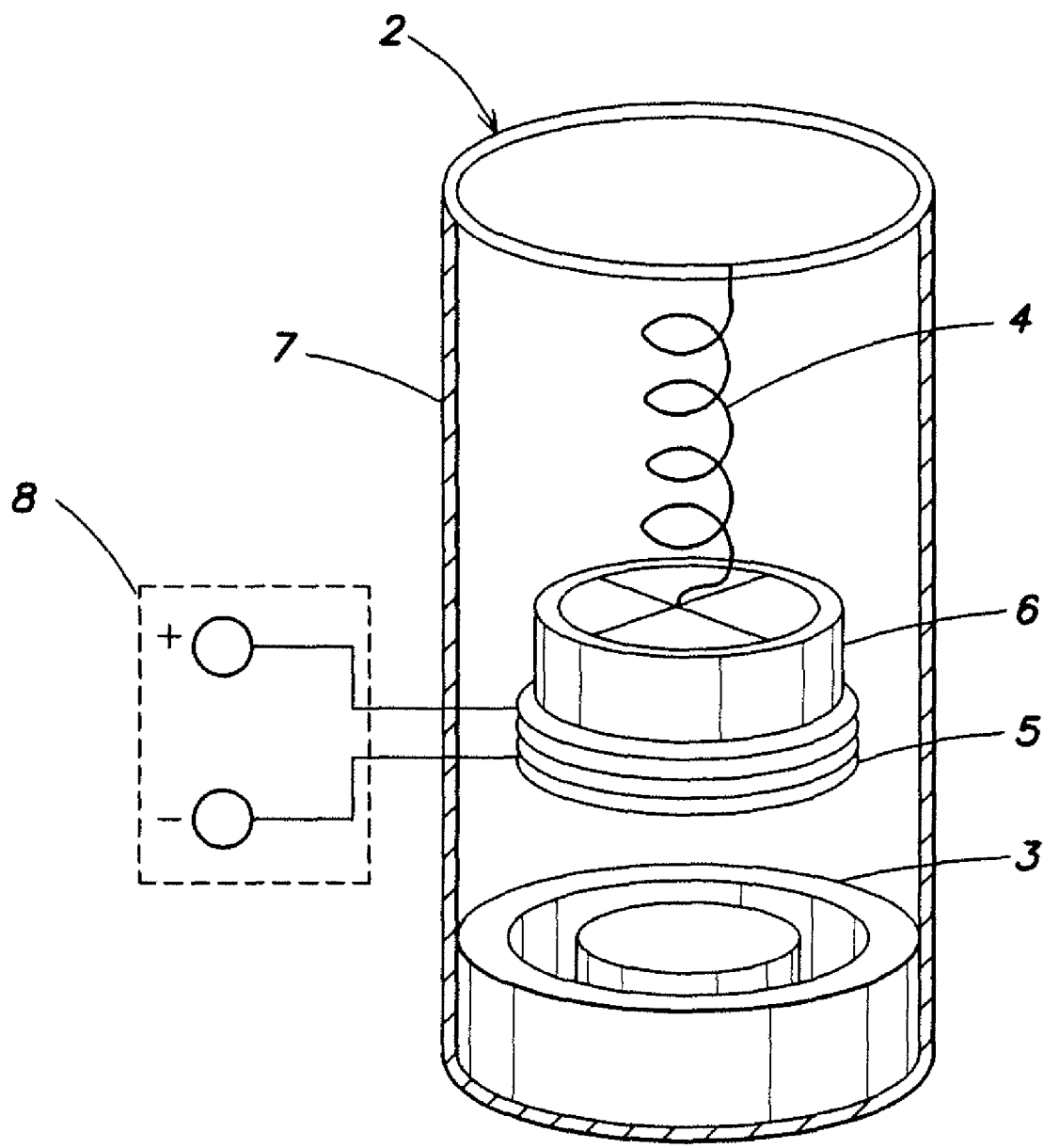
FIG. 1 is a block schematic diagram of a prior art energy harvester device having a permanent magnet and inertial mass.
Figure 2:
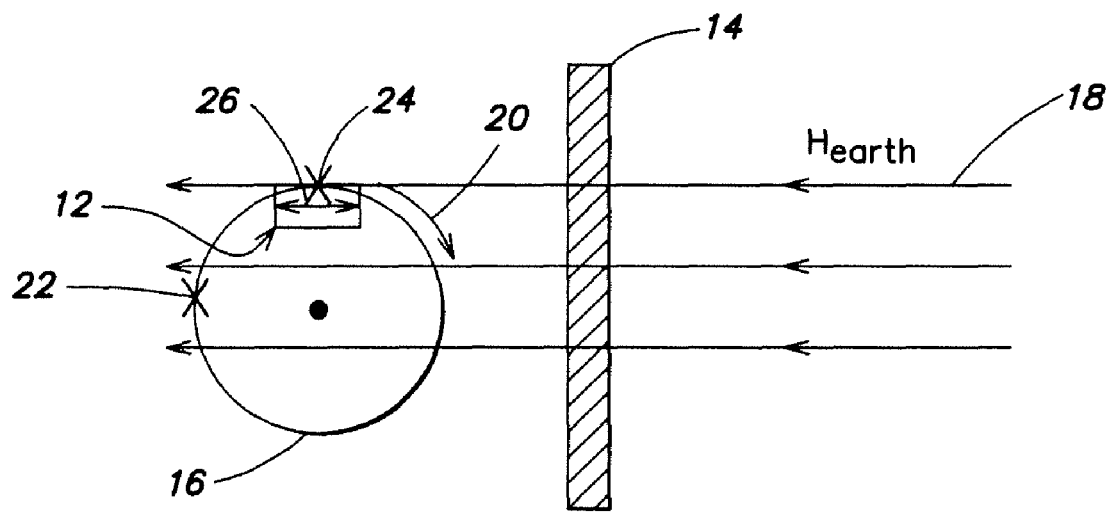
FIG. 2 is a schematic diagram of an energy harvester according to one embodiment of the invention, in which the harvester is attached to a moving part and is actuated by its motion in the earth's magnetic field.

FIG. 2 illustrates a first embodiment of an energy harvester device according to the invention, wherein a static external magnetic field, here $H_{earth}$ (the earth's magnetic field), acts at a distance (or through a non-magnetic barrier) on a sensor whose orientation in the field changes with time. Thus, the flux density in the sensor is altered by changes in the physical orientation of the sensor with respect to the direction of the earth's field (or other substantially static field). FIG. 2 illustrates this with a non-magnetic barrier 14 separating the energy harvester 12 on the left, attached to a moving object (rotating machinery part 16), from the source of external field 18 on the right. The arrow 26 extending across the width of sensor 12 represents the plane of the magnetization vector M. The arrow 20 illustrates rotation of sensor 12 from a first position 22 (labeled X) to a second position 24 (labeled X'). Alternatively, the sensor can be attached to a rotating part on a vehicle, a door, or other object that moves relative to the earth's field. As a further alternative, the sensor may also be suspended on its axis such that linear vibration acting on the sensor changes its orientation in the earth's field. The change in sensor orientation requires some asymmetry in the suspension for the vibrations to cause rotation of sensor about its axis. It is preferable that the change in sensor orientation be such that the axis between its electrodes changes orientation relative to the static field direction. In other words, the sensor motion should preferably not be rotation about the axis of the applied field.

Figure 3:
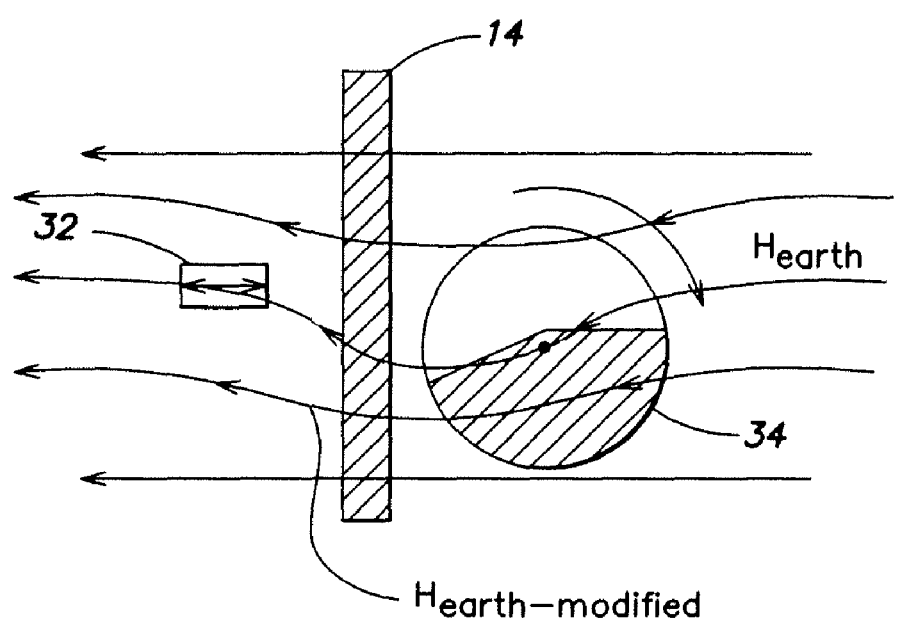
FIG. 3 is a schematic diagram of another embodiment of the energy harvester of the invention, in which a stationary harvester is actuated by a changing external field ($H_{earth-modified}$), the external field being that of the earth's field changed in magnitude or direction by a moving object in its path.

A second embodiment of the invention is shown in FIG. 3, wherein a changing external field, $H_{earth-modified}$, acts at a distance (or through a non-magnetic barrier) on a stationary sensor 32. Here the orientation of the field at the sensor location changes with time. In FIG. 3, a moving magnetic object (rotating disk 34) in the path of the earth's ambient field causes a change in that field, and this changing field ($H_{earth-modified}$) then reaches (acts on) the static sensor 32.

Figure 4:
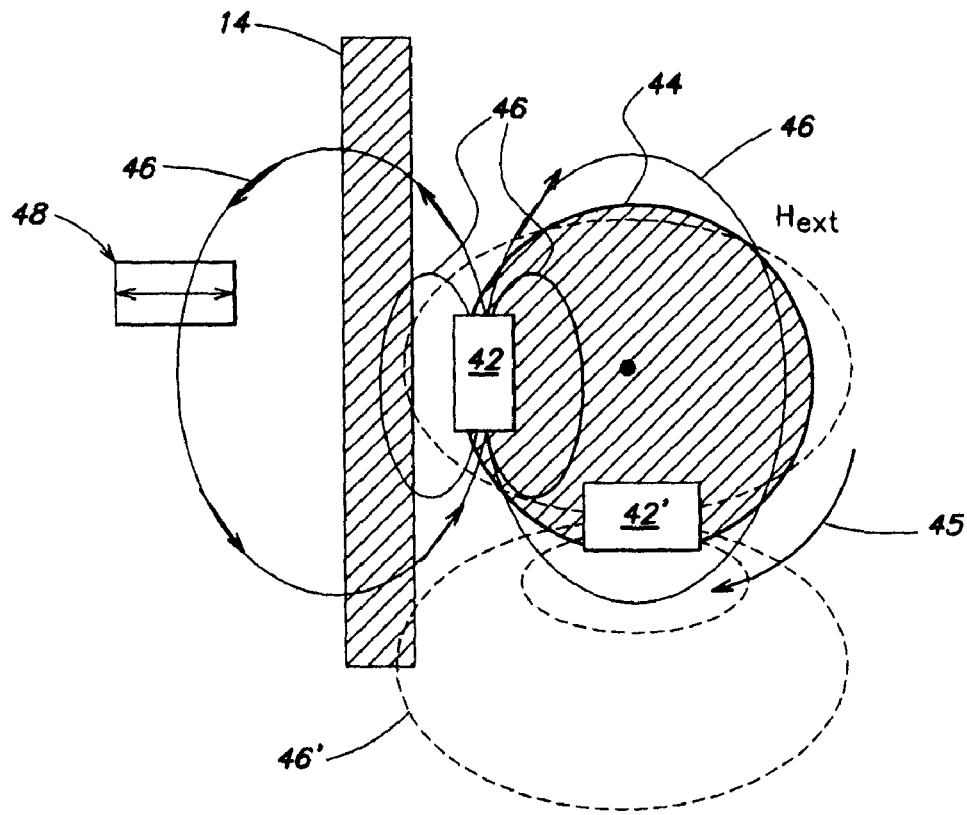
FIG. 4 is a schematic diagram of another embodiment of the invention in which a stationary harvester device is activated by a remote external changing magnetic field $H_{ext}$, where $H_{ext}$ is due to a permanent magnet affixed to a moving part exterior to the harvester.

In a further alternative embodiment, shown in FIG. 4, a permanent magnet 42 is affixed to a rotating or moving object 44 remote from the sensor 48. The change in position of the magnet 42 relative to the stationary sensor 48 causes a changing field (see field lines 46 of $H_{ext}$) that acts on the static sensor 48. Arrow 45 illustrates rotation of the magnet to a second position (shaded area 42' at the bottom of rotating disk 44) and the changing field as dashed lines 46'. Other sources of changing or alternating magnetic field can be found near electrical transformers, motors, actuators, switches, many electronic devices, inductor wires or coils, and near areas of high vehicle traffic or moving machinery. The remote changing magnetic field source can be designed to couple with the sensor efficiently in terms of frequency, distance and magnitude to deliver power remotely to the sensor.

Figure 5:
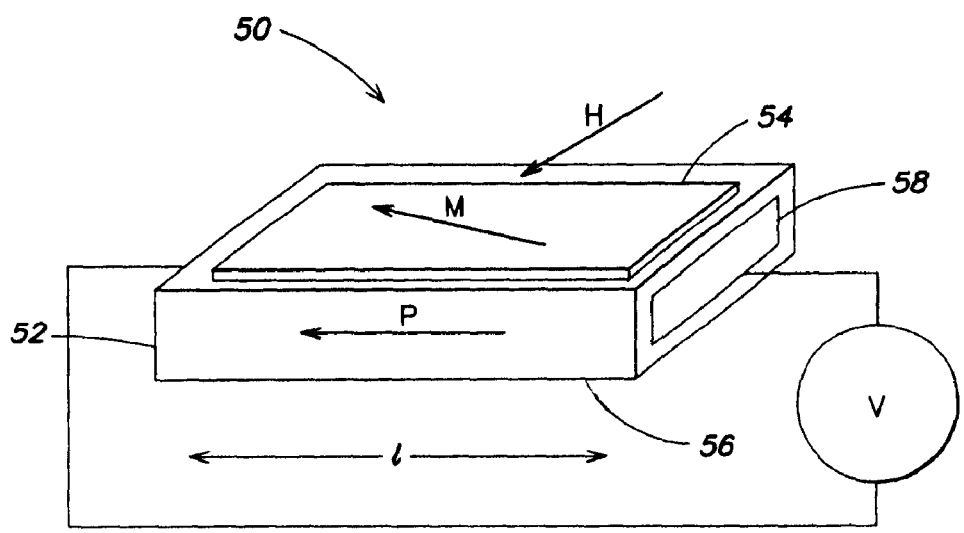
FIG. 5 is a schematic diagram of one construction of a sensing element useful in the present invention.

FIG. 5 is a schematic illustration of a preferred sensor configuration 50 for use in the present invention. In this embodiment, a central layer of an electroactive (e.g., ceramic, polymer or single crystal piezoelectric; or a relaxor ferroelectric) material having a polarization vector P is shown, sandwiched between two layers 54, 56 of magnetostrictive material (e.g., of a soft ferromagnetic material having a non-zero magnetostriction) on opposing faces of central layer 52. Each magnetostrictive layer has a magnetization vector M which is caused to rotate in the plane of the magnetostrictive layer by an applied field H. A pair of electrodes 58 are disposed at opposite ends of the piezoelectric, the axis between the electrodes being parallel to the plane in which the magnetization vectors rotate. The voltage V generated in the piezoelectric, resulting from the magnetoelastic stress generated in the magnetic layers and transferred to the piezoelectric, can be measured in a circuit coupled to the electrodes attached to the piezoelectric layers.

The materials and configuration of the sensor may vary depending upon the particular application. While it is generally desirable to use a magnetic material with large magnetostriction for the magnetic layer(s), it is generally more important (for optimum power delivery) that the magnetostrictive material have a large product of a magnetostrictive stress and stiffness modulus (see "Novel Sensors Based on Magnetostrictive/Piezoelectric Lamination," J. K. Huang, D. Bono and R. C. O'Handley, Sensors and Actuators 2006). This insures that the magnetic layer(s) more effectively transfer stress to the piezoelectric material. For example, while FeCo(Hyperco) shows a relatively large magnetostriction (approaching 100 ppm) and is extremely stiff, the product of these parameters translates to a magnetostrictive stress of 1.2 MPa. A high-magnetostriction material such as $Fe_2(Dy_{2/3}Tb_{1/3})$ (known as Terfenol-D) on the other hand, is mechanically softer than FeCo but shows a much larger magnetostrictive strain and its magnetostrictive stress approaches 6 MPa.

It is also important (for optimum power generation) that the magnetostrictive stress changes by the largest possible amount under the influence of the changing field strength available at the sensor. For example, the magnetization vector of FeCo can be rotated in a field of a few tens of Oe (Oersteds) while the magnetization vector of Terfenol-D can be rotated in a field of several hundreds of Oe, provided in each case they are properly annealed and the aspect ratio of the material in the magnetizing direction is favorable.

The class of magnetostrictive materials that can be magnetized in the weakest fields consist of a variety of amorphous alloys based on iron (Fe) (optionally in combination with nickel (Ni)) and with glass formers such as boron (B) (optionally with silicon (Si)).

Electro-active materials, such as the commercially available piezoelectric lead-zirconate-titanates (PZT) have stress-voltage coefficients, $g_{13}$ and $g_{33}$, with values approximately equal to 10 and 24 mV/(Pa-m), respectively. Thus, a stress applied to the piezoelectric parallel to the direction across which the voltage is measured is more effective in generating a voltage than a stress transverse to this direction (out of the plane in which the vector is rotated by the field). Further, relaxor ferroelectrics have $g_{ij}$ values that can be three to four times those of piezoelectrics. Also useful in these applications are piezo fibers or manufactured piezo fiber composites. They may have interdigitated electrodes with various spacings to produce electric fields along the piezo fibers or they may be electroded across the thickness of the fibers. Polymeric piezoelectric material(s) (e.g., poly-vinylidene-difluoride PVDF) may be advantageous in some applications.

There are a number of ways to increase the strength of the earth's field entering the magnetostrictive layers so as to enhance the power harvested. One way is to use flux concentrators (e.g., fan-shaped soft magnetic layers) placed in series with the sensing element in the presence of the field.

Figure 6:
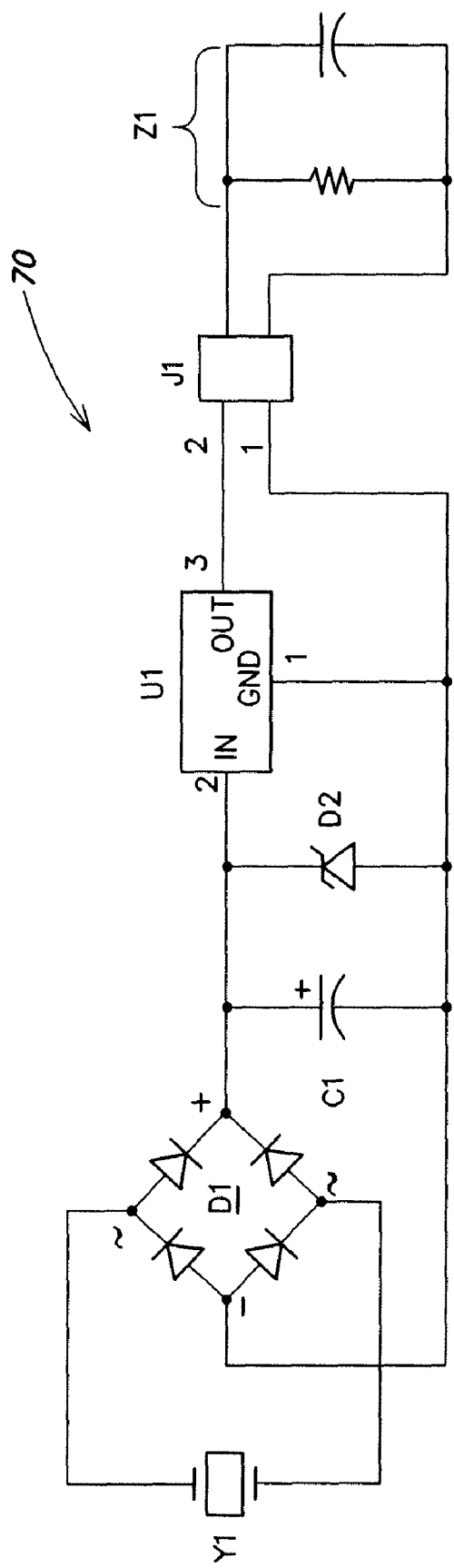
FIG. 6 is a schematic diagram of a circuit for converting and changing electrical output of the harvester to a DC electrical signal, conditioning, storing and providing the resutling electrical energy to a load.

The sensor output can be adapted for immediate use or storage by coupling the sensor to an electronic circuit. One such circuit 70 is shown in FIG. 6. On the left hand side, a PME energy harvester Y1 is shown. A diode bridge D1 is disposed in parallel across the harvester output. The full wave diode bridge converts the AC electric charge on the harvester to a DC charge. Connected in parallel to the diode bridge is an energy storage capacitor C1 which stores the harvested energy as a voltage across it. Parallel to the capacitor is a limiter zener diode D2 which prevents overcharging of the capacitor C1 beyond its breakdown voltage. Next provided in parallel to the capacitor and diode bridge is a voltage regulator U1. The voltage regulating circuit reduces the capacitor voltage to a useful level for a load. The voltage regulated output across J1 is applied to the load, here represented as a load impedance Z1, which typically includes resistive and capacitive elements, and which uses the harvested energy to do useful work.

Figure 7:
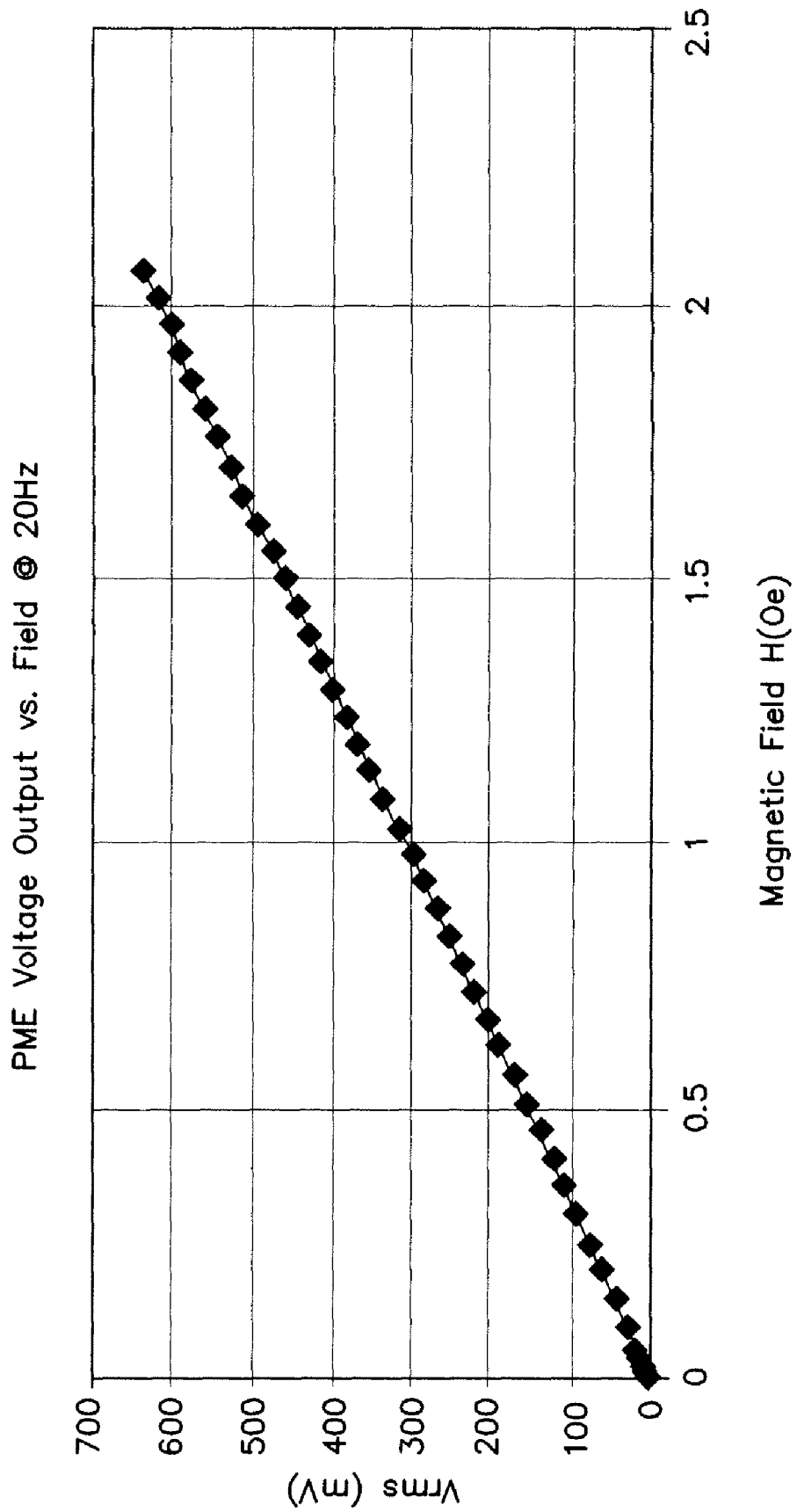
FIG. 7 is a graph of PME voltage output versus field at 20 Hz for one embodiment of the invention.

FIG. 7 is a comparison of the PME output voltage signal (RMS voltage in millivolts) versus magnetic field strength (H in telsa). In this embodiment the changing external magnetic field is at a low frequency of 20 Hz. The PME voltage output linearly increases from 0 to 650 millivolts with increasing magnetic field strength from 0 to 2 Oe. Alternatively, the magnetic field can be static and the position of the PME varying. The substantially linear relationship between the PME voltage output and magnetic filed strength is representative for low frequency applications (where the field changes or the sensor motions are at low vibration frequencies or power transmission frequencies).

Figure 8A:
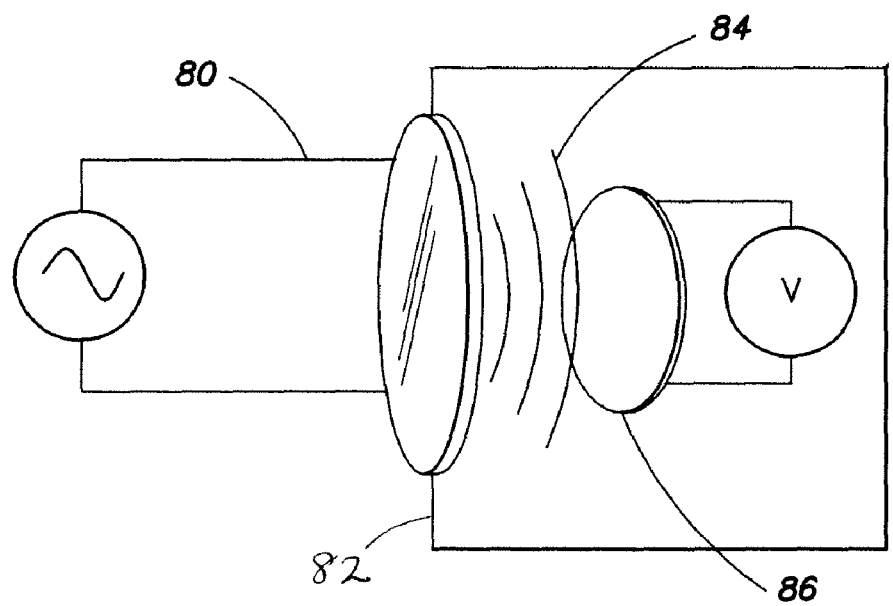
FIGS. 8a-8b are schematic diagrams of two embodiments of an energy harvester wherein an external changing magnetic field generated by a coil is transmitted through tissue to an embedded PME sensor.
Figure 8B:
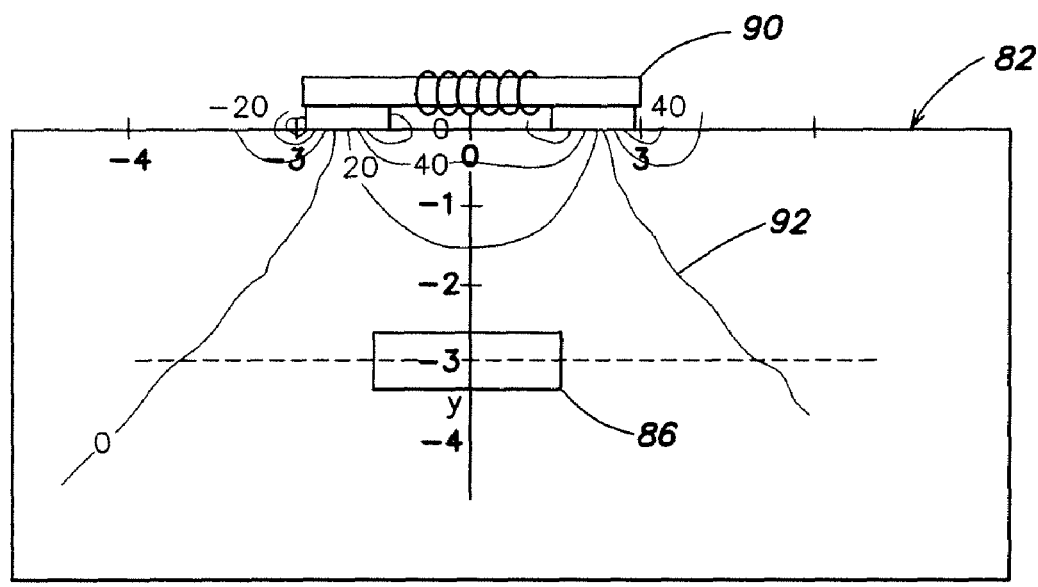

Alternatively, a higher frequency external field can be used to obtain a greater level of power from the PME (compared to the low frequency operation of FIG. 7). This is illustrated with the embodiment and resulting power output shown in FIGS. 8-9. FIG. 8a illustrates a means of delivering power inside a living organism (or any inaccessible or difficult to access location) without requiring the use of electrical wiring between the source of the power and the target device and without requiring (or with diminished need for) batteries. FIG. 8a shows an external loop antenna 80 generating an alternating magnetic field outside of the body. The magnetic field 84 generated by this loop antenna is transmitted through the skin and other tissue 82 to an embedded PME sensor 86 producing a resulting output voltage V. The power transmission here is achieved not by a high frequency microwave, RF or other electromagnetic wave, but rather by means of a relatively low frequency, benign, alternating magnetic field. Microwaves and other electromagnetic waves having a wavelength comparable to or less than the distance between the source and receiver, are rapidly attenuated by water or metals, and thus would not be suitable in this application. Instead, the loop antenna produces a low-frequency, magnetic-rich waves which are left essentially unattenuated by tissue (assuming no intervening magnetic material), and which do not have problems with tissue heating that accompanies microwaves. Alternatively, instead of a loop antenna (with no core) the external source could be a core-filled coil antenna such as a solenoid coil with core 90 (FIG. 8b), wherein the core may significantly enhance the field 92 in the body The field generated by a loop, solenoid or core-filled coil antenna is richer in magnetic field strength than electric field strength within a range comparable to the wavelength of the radiation. The wavelength is given by the equation $\lambda=c/f$, where c is the speed of light in the medium, and f is the frequency of the radiation. At 1 MHZ (megahertz) in air, $\lambda$ equals 300 m (meters); at 100 MHZ, $\lambda$ equals 3 m. Thus, there is a wide range of frequencies over which to transmit a magnetic-field rich electromagnetic wave without significant attenuation.

The implanted passive magnetostrictive/electroactive (PME) sensor/transducer 86 receives and converts the AC magnetic field 84 to an AC voltage that can be processed to produce power needed for a particular application. For example, this apparatus can be used in powering internal pumps, sensors, valves and transponders in human and animals. More generally, it can be used to power devices which monitor health, organ function or medication needs, and for performing active functions such as pumping, valving, stimulation of cell growth or accelerated drug or radiation treatment locally. The described means of delivering power inside a living organism can be achieved without the use of electrical wires in between the source of the power and the target device and without the need, or diminished need, for batteries.

Figure 9:
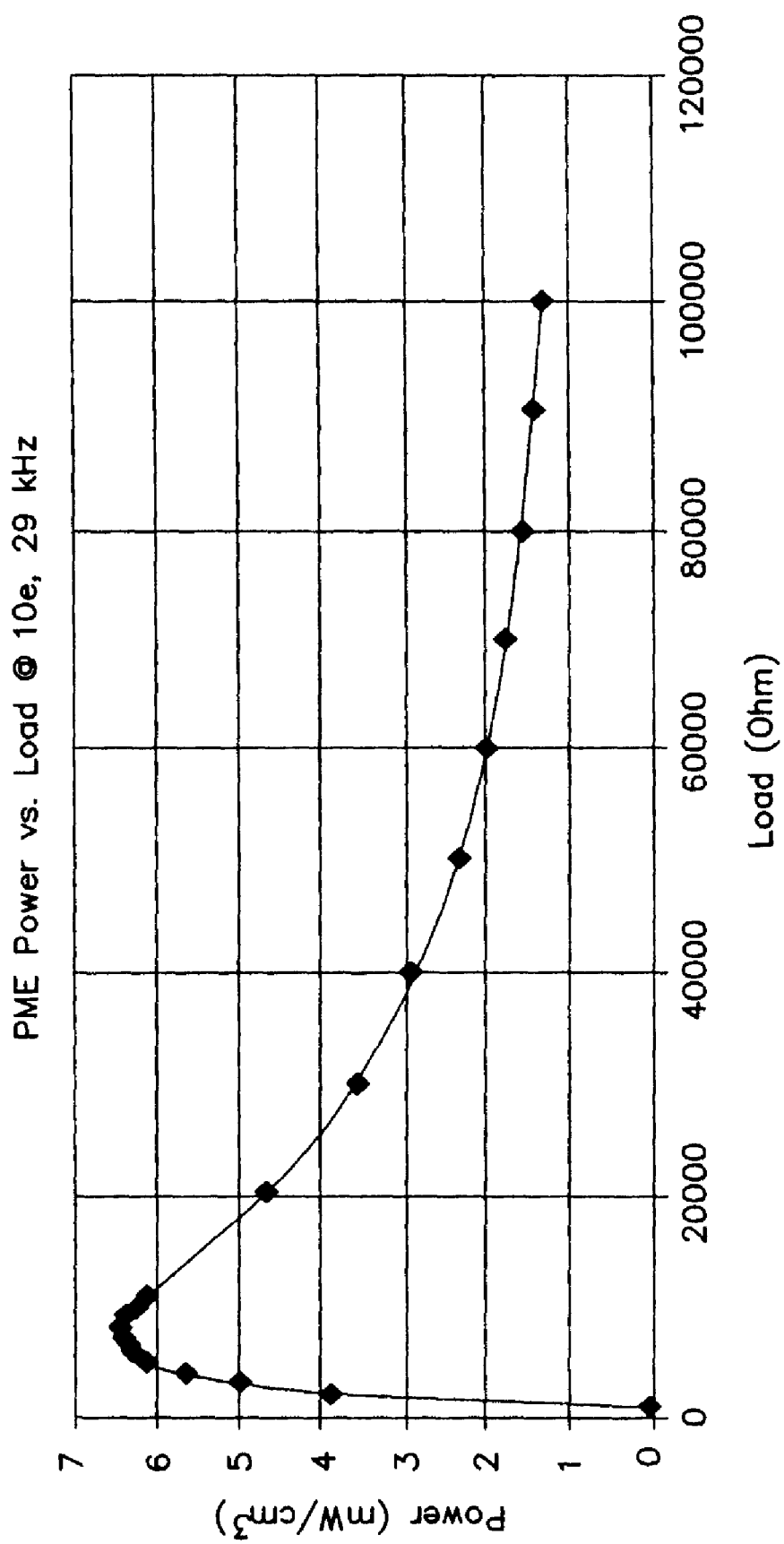
FIG. 9 is a graph of PME power versus load at 1 Oe and 29 kHz according to another embodiment of the invention.

The wireless power harvested for the remote application can be optimized, for example, if resonance is achieved at each stage of transduction. Thus the external power source and the transmit antenna should be in resonance. The PME device should also be in resonance with the field it responds to, and the PME device should also be in resonance with the part of the circuit that receives the signal from the PME device. By careful design and material selection, it is possible for all three resonances to closely coincide. FIG. 9 illustrates one example of a PME power output (mW/cm³) versus load (ohm) for one such resonant system operating at a frequency of 29 kHz and a field of one (1) Oe.

The remote sensor can be used not only for powering internal pumps, sensors and transponders in humans and animals, but can be used to monitor the flow of things (people or inanimate objects) past gates (either for security or tracking purposed).

There will now be described in more detail alternative sensor configurations and sensor materials which may be useful in various embodiments or the present invention.

Figure 10:
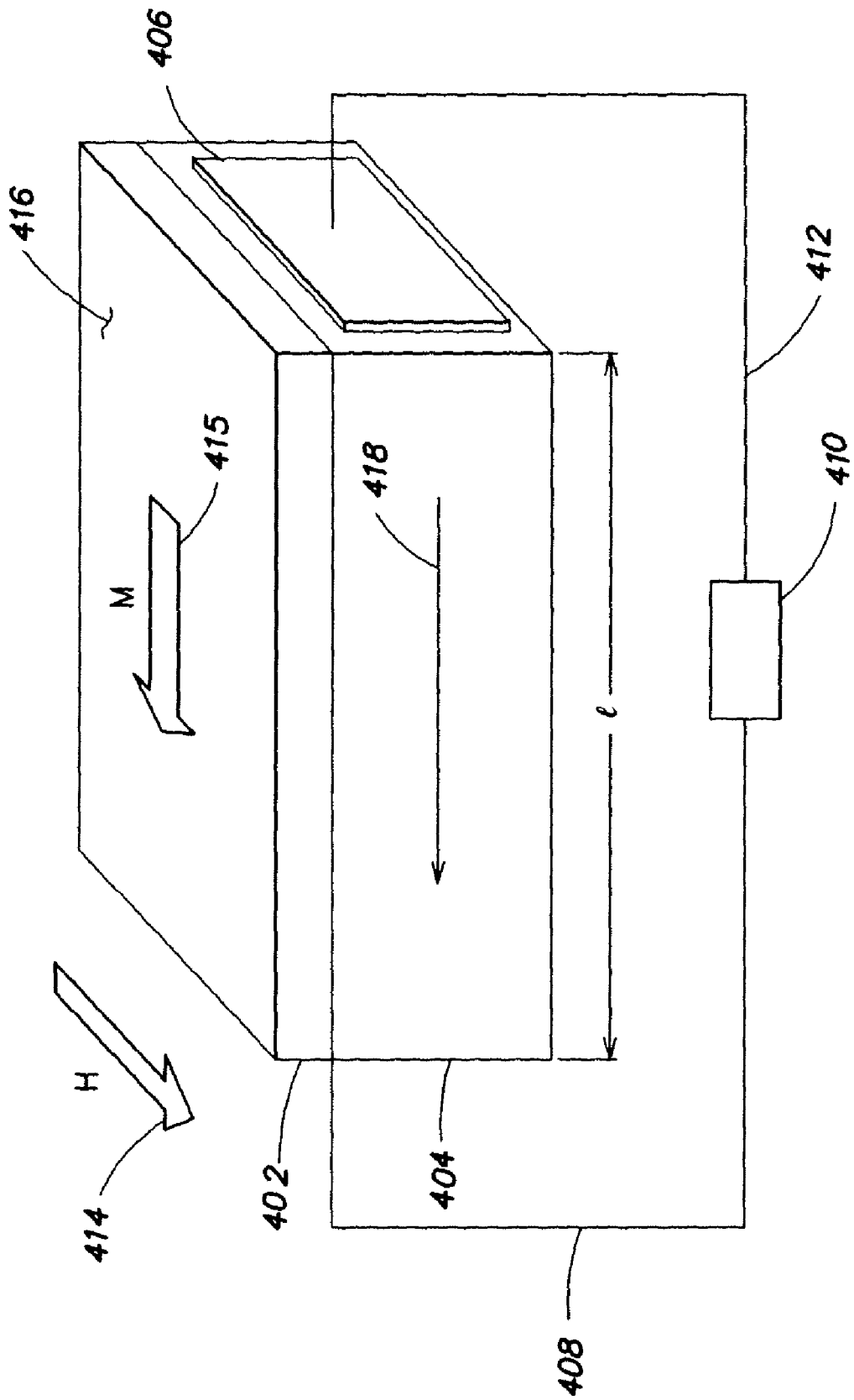
FIG. 10 is a block schematic diagram of a passive magnetostrictive/electroactive sensor constructed in accordance with one embodiment of the invention.

FIG. 10 is a block schematic diagram of one embodiment of a passive magnetostrictive sensor useful in the practice of the invention. The sensor 400 comprises a magnetic layer 402 that is bonded to a piezoelectric layer 404 by a suitable non-conductive means, such as non-conductive epoxy glue. Although only one magnetic layer 402 is shown bonded to a single piezoelectric layer 404, those skilled in the art would understand that two or more magnetic layers can be used. The magnetization vector 415 (M) of the magnetic material 402 rotates in the plane 416 of the magnetic layer 402 when an external magnetic field (H) is applied as shown by the arrow 414. The rotation of the magnetization vector M causes a stress in the magnetostrictive layer 402 which is, in turn, applied to the piezoelectric layer 404 to which the magnetic layer 402 is bonded. In this design the direction of magnetization, M, rotates in the preferred plane of magnetization, changing direction from being parallel to perpendicular (or vice versa) to a line joining the electrodes. This maximizes the stress change transferred to the electroactive element.

The stress-induced voltage in the piezoelectric material 404 is measured across a pair of electrodes 406 and 407 of which only electrode 406 is shown in FIG. 10. The magnitude of the voltage developed across electrodes 406 and 407 is a function of the magnetic field strength for $H<H_a$, the anisotropy field (at which M is parallel to the applied field) and can be utilized to power a device 410 that is connected to electrodes 406 and 407 by conductors 412 and 408, respectively.

The sensor is constructed so that stress-induced voltage is measured in a direction that is parallel to the plane 416 in which the magnetization rotates. The stress is generated in the magnetic material 402, which responds to an external magnetic field 414 (H) with a magnetoelastic stress, $\sigma_{mag}$, that has a value in the approximate range of 10 to 60 MPa. Because the magnetic material 402 is bonded to a piezoelectric layer 404, the layer 404 responds to the magnetostrictive stress with a voltage proportional to the stress, $\sigma_{mag}$, transmitted to it. Piezoelectric materials respond to a stress with a voltage, V, that is a function of the applied stress, a voltage-stress constant, $g_{ij}$, and the distance, l between the electrodes. In particular, $$\delta V = g_{ij}^{piezo} \delta \sigma_{mag} l$$

Here $\delta\sigma_{mag}$ is the change in magnetic stress that is generated in the magnetic material by the field-induced change in its magnetization direction. A fraction, $f$, of this stress is transferred to the electroactive element. $\delta V$ is the resulting stress-induced change in voltage across the electrodes on the electroactive element.

If the voltage is measured in a direction orthogonal to the direction in which the stress changes, then $g_{ij}=g_{13}$. As mentioned previously, typically piezoelectric values for $g_{13}$ are 10 millivolt/(meter-Pa). However, if the voltage is measured in a direction parallel to the principal direction in which the stress changes in accordance with the embodiment of FIG. 4, then $g_{ij}=g_{33}$ Thus, the sensor operates in a $g_{33}$ or $d_{33}$ mode. For a typical piezoelectric material $g_{33}$=24 millivolt/(meter-Pa)= 0.024 volt-meter/Newton. In this case, a stress of 1 MPa generates an electric field of 24 kilovolt/meter. This field generates a voltage of 240 V across a 1 cm (l=0.01 m) wide piezoelectric layer.

The stress generated by the magnetic material 402 depends on the extent of rotation of its magnetization, a 90 degree rotation producing the full magnetoelastic stress. The extent of the rotation, in turn, depends of the angle between the magnetization vector 415 and the applied magnetic field direction 414 and also depends on the strength of the magnetic field and on the strength of the magnetic anisotropy (magnetocrystalline, shape and stress-induced) in the magnetic layer. The fraction, $f$, of the magnetostrictive stress, $\sigma_{mag}$, transferred from magnetic to the piezoelectric layer depends on the (stiffness×thickness) product of the magnetic material, the effective mechanical impedance of the bond between the magnetic and electric elements (proportional to its stiffness/thickness), and the inverse of the (stiffness×thickness) of the piezoelectric layer.

A quality factor may be defined from the above equation to indicate the sensitivity of the device, that is, the voltage output per unit magnetic field, H (Volts-m/A):

$$\frac{\partial V}{\partial H} = g_{33}^{piezo} f \left( \frac{\partial \sigma_{mag}}{\partial H} \right) l$$

The characteristics of a suitable magnetostrictive material are preferably large internal magnetic stress change as the magnetization direction is changed. This stress is governed by the magnetoelastic coupling coefficient, $B_1$, which, in an unconstrained sample, produces the magnetostrictive strain or magnetostriction, $\lambda$, proportional to $B_1$ and inversely proportional to the elastic modulus of the material. It is also important that the magnetization direction of the magnetic material can be rotated by a magnetic field of magnitude comparable to the applied field. In general, the magnetic material should also be mechanically robust, relatively stable (not prone to corrosion or decomposition), and receptive to adhesives. In addition, if the magnetic material is electrically non-conducting, it can be bonded to the electroactive element with the thinnest non-conducting adhesive layer that provides the needed strength without danger of shorting out the stress-induced voltage developed across the electroactive element. For PME devices in which the voltage is measured across electrodes that are not the same as the megnetostrictive layers, care must be taken that the magnetostrictive layers not short out the voltage between the measuring electrodes. This can be accomplished by using a non-conducting adhesive to insulate the magneostrictive layer(s) from the electroactive element(s).

Many known magnetostrictive materials can be used for the magnetic layer 402. These include various magnetic alloys, such as amorphous-FeBSi or Fe—Co—B—Si alloys, as well as polycrystalline nickel, iron-nickel alloys, or iron-cobalt alloys such as $Fe_{50}Co_{50}$ (Hyperco). For example, amorphous iron and/or nickel boron-silicon alloys of the form $Fe_xB_ySi_{1-x-y}$, where 70<x<86 at %, 2<y<20, and 0<z=1−x−y<8 at % are suitable for use with the invention with a preferred composition near $Fe_{78}B_{20}Si_2$. Also suitable are alloys of the form $Fe_xCo_yB_zSi_{1-x-y-z}$ where 70<x+y<86 at % and y is between 1 and 46 at %, 2<z<18, and 0<1−x−y−z<16 at %, with a preferred composition near $Fe_{68}Co_{10}B_{18}Si_4$. Iron-nickel alloys with Ni between 40 and 70 at % with a preferred composition near 50% Ni can be used. Similarly, iron-cobalt alloys with Co between 30 and 80% and a preferred composition near 55% Co (such as $Fe_{50}Co_{50}$.) are also suitable.

Another magnetostrictive material that is also suitable for use with the invention is Terfenol-D®($Tb_x Dy_{1-x} Fe_y$), an alloy of rare earth elements Dysprosium and Terbium with the transition metal iron, manufactured by ETREMA Products, Inc., 2500 N. Loop Drive, Ames, Iowa 50010, among others. Terfenol-D® can generate a maximum stress on the order of 60 MPa for a 90-degree rotation of its magnetization. Such a rotation can be accomplished by an external applied magnetic field on the order of 400 to 1000 Oersteds (Oe). Also useful are highly magnetostrictive alloys such as Galfenol®, $Fe_{1-x}Ga_x$. (ETREMA Products). Softer magnetic materials, such as certain Fe-rich amorphous alloys mentioned above, may achieve full rotation of magnetization in fields of order 10 Oe, making them suitable for the magnetic layer in a sensor for sensing weaker fields. Finally, it is possible to use certain so-called nanocrystalline magnetic materials. In these polycrystalline materials, it is generally that case that the magnetization can be rotated as easily as it can be in amorphous materials. But nanocrystalline materials can sometimes be engineered to have larger magnetoelastic coupling coefficients than amorphous materials.

The preferred characteristics of a suitable electroactive layer for the sensor devices are primarily that they have a large stress-voltage coupling coefficient, $g_{33}$. In addition, they preferably should be mechanically robust, receptive to adhesives, not degrade the metallic electrodes that must be placed on them (this is most often easily achieved when the electrodes are made of noble metals, such as silver or gold). Generally, the electroactive material is chosen on the basis of having a value of $g_{ij}$ greater than 10 mV/(Pa-m).

The electroactive layer can be a ceramic piezoelectric material such as lead zirconate titanate $Pb(Zr_xTi_{1-x})O_3$, or variations thereof, aluminum nitride (AlN) or simply quartz, $SiO_X$. In some applications a single crystal (as opposed to a ceramic or polycrystalline) piezoelectric material may be advantageous. Alternatively, a polymeric piezoelectric material such as polyvinylidene difluoride (PVDF) would be suitable for applications where the stress transferred from the magnetostrictive material is relatively weak. The softness of the polymer will allow it to be strained significantly under weaker applied stress to produce a useful polarization, or voltage across its electrodes. It is also advantageous in some applications to use another electroactive material, such as an electrostrictive material (for example, $(Bi_{0.5}Na_{0.5})_{1-x}Ba_xZr_yTi_{1-y}O_3$) or a relaxor ferroelectric material (for example, $Pb(Mg_{1/3}Nb_{2/3})_3$). Collectively, the piezoelectric, ferroelectric, electrostrictive and relaxor ferroelectric layers are called "electroactive" layers.

Piezoelectric materials typically have $g_{33} \sim 4 \times g_{31}$ and $g_{33} \approx 20$ to 30 mV/(Pa-m) which is about $10 \times d_{31}$. For PVDF, $g_{33} \approx 100$ mV/(Pa-m) and some relaxor ferroelectrics can have $g_{22} \approx 60$ mv/(Pa-m).

Model predictions and experimental results shown in Table 1 compares the parameters $g_{ij}$, in mV/m-Pa, the electrode spacing 1 in meters, the maximum stress per unit field $(B_1/\mu_o H_a)$ in Pa/T, and calculated field sensitivity in nV/nT and the observed field sensitivity, dV/dB. The values tabulated for a $g_{33}$ device using a relaxor ferroelectric are based on the data observed with a piezoelectric based sensor and using a ratio of $g_{33}$ for typical relaxors/piezoelectrics.

TABLE 1

| | | | max. | Sensitivity | |
| --- | --- | --- | --- | --- | --- |
| | $g_{ij}$ | l | stress | Calc. | Obs. |
| Piezo/magnetic sensors: | | | | | |
| $d_{31}$ sensor | 11 | $10^{-3}$ | $10^8$ | $10^4$ | 280 |
| $d_{31}$ sensor | 11 | $10^{-3}$ | $10^8$ | $10^4$ | 1,200 |
| $d_{33}$ sensor | 24 | $10^{-2}$ | $10^9$ | $2 \times 10^5$ | $1.5 \times 10^4$ |
| Relaxor/magnetic sensors: | | | | | |
| $d_{33}$ relaxor/mag sensor | 60 | $10^{-2}$ | $10^9$ | $10^6$ | ($10^5$) |

The calculated sensitivity in the table is defined with perfect stress coupling, namely $f=1$ in MKS units (V/Tesla) as $$\frac{\partial V}{\mu_o \partial H} \approx g_{33}^{piezo} \ell \frac{B_1}{\mu_o H_a}$$

Here $B_1$ is the magneoelastic coupling coefficient, a material constant that generates the magnetic stress in the magnetostrictive material, $\sigma_m$, which was used in earlier equations.

Other useful sensor embodiments are disclosed in U.S. Ser. No. 10/730,355 filed 8 Dec. 2003 entitled "High Sensitivity, Passive Magnetic Field Sensor and Method of Manufacture," by J. Huang, et al., the subject matter of which is incorporated by reference herein in its entirety.

Medical Background of the Invention

Chronic pain is usually a multidimensional phenomenon involving complex physiological and emotional interactions. For instance, one type of chronic pain, complex regional pain syndrome (CRPS)—which includes the disorder formerly referred to as reflex sympathetic dystrophy (RSD)—most often occurs after an injury, such as a bone fracture. The pain is considered "complex regional" since it is located in one region of the body (such as an arm or leg), yet can spread to additional areas. Since CRPS typically affects the sympathetic nervous system, which in turn affects all tissue levels (skin, bone, etc.), many symptoms may occur. Pain is the main symptom. Other symptoms vary, but can include loss of function, temperature changes, swelling, sensitivity to touch, and skin changes.

Another type of chronic pain, failed back surgery syndrome (FBSS), refers to patients who have undergone one or more surgical procedures and continue to experience pain. Included in this condition are recurring disc herniation, epidural scarring, and injured nerve roots.

Arachnoiditis, a disease that occurs when the membrane in direct contact with the spinal fluid becomes inflamed, causes chronic pain by pressing on the nerves. It is unclear what causes this condition.

Yet another cause of chronic pain is inflammation and degeneration of peripheral nerves, called neuropathy. This condition is a common complication of diabetes, affecting 60%-70% of diabetics. Pain in the lower limbs is a common symptom.

An estimated 10% of gynecological visits involve a complaint of chronic pelvic pain. In approximately one-third of patients with chronic pelvic pain, no identifiable cause is ever found, even with procedures as invasive as exploratory laparotomy. Such patients are treated symptomatically for their pain.

A multitude of other diseases and conditions cause chronic pain, including postherpetic neuralgia and fibromyalgia syndrome. Neurostimulation of spinal nerves, nerve roots, and the spinal cord has been demonstrated to provide symptomatic treatment in patients with intractable chronic pain.

Many other examples of chronic pain exist, as chronic pain may occur in any area of the body. For many sufferers, no cause is ever found. Thus, many types of chronic pain are treated symptomatically. For instance, many people suffer from chronic headaches/migraine and/or facial pain. As with other types of chronic pain, if the underlying cause is found, the cause may or may not be treatable. Alternatively, treatment may be only to relieve the pain.

Chronic pain, though the primary indication for neurostimulation, is not the only disease entity in the human body that can benefit from neuromodulation. Treatment of acute stroke, sleep apnea, cancer, migraines, bone and joint disease and various types of primary brain disorders such as depression, epilepsy and mood disorders would benefit greatly from neuromodulation. These therapeutic areas are currently being researched heavily.

All of the devices currently available for producing therapeutic stimulation have drawbacks. Many are large devices that must apply stimulation transcutaneously. For instance, transcutaneous electrical nerve stimulation (TENS) is used to modulate the stimulus transmissions by which pain is felt by applying low-voltage electrical stimulation to large peripheral nerve fibers via electrodes placed on the skin. TENS devices can produce significant discomfort and can only be used intermittently.

Other devices require that a needle electrode(s) be inserted through the skin during stimulation sessions. These devices may only be used acutely, and may cause significant discomfort.

Implantable, chronic stimulation devices are available, but these currently require a significant surgical procedure for implantation. Surgically implanted stimulators, such as spinal cord stimulators, have been described in the art. These spinal cord stimulators have different forms, but are usually comprised of an implantable control module to which is connected a series of leads that must be routed to nerve bundles in the spinal cord, to nerve roots and/or spinal nerves emanating from the spinal cord, or to peripheral nerves. The implantable devices are relatively large and expensive. In addition, they require significant surgical procedures for placement of electrodes, leads, and processing units. These devices may also require an external apparatus that needs to be strapped or otherwise affixed to the skin. Drawbacks, such as size (of internal and/or external components), discomfort, inconvenience, complex surgical procedures, and/or only acute or intermittent use has generally confined their use to patients with severe symptoms and the capacity to finance the surgery.

There are a number of theories regarding how stimulation therapies such as Transcoutaneous electrical neuro-stimulation (TENS) machines and spinal cord stimulators may inhibit or relieve pain. The most common theory—gate theory or gate control theory—suggests that stimulation of fast conducting nerves that travel to the spinal cord produces signals that "beat" slower pain-carrying nerve signals and, therefore, override/prevent the message of pain from reaching the spinal cord. Thus, the stimulation closes the "gate" of entry to the spinal cord. It is believed that small diameter nerve fibers carry the relatively slower-traveling pain signals, while large diameter fibers carry signals of e.g., touch that travel more quickly to the brain.

Spinal cord stimulation (also called dorsal column stimulation) is best suited for back and lower extremity pain related to adhesive arachnoiditis, FBSS, causalgia, phantom limb and stump pain, and ischemic pain. Spinal cord stimulation is thought to relieve pain through the gate control theory described above. Thus, applying a direct physical or electrical stimulus to the larger diameter nerve fibers of the spinal cord should, in effect, block pain signals from traveling to the patient's brain. In 1967, Shealy and coworkers first utilized this concept, proposing to place stimulating electrodes over the dorsal columns of the spinal cord. (See Shealy C. N., Mortimer J. T., Reswick, J. B., "Electrical Inhibition of Pain by Stimulation of the Dorsal Column", in Anesthesia and Analgesia, 1967, volume 46, pages 489-491.) Since then, improvements in hardware and patient selection have improved results with this procedure.

The gate control theory has always been controversial, as there are certain conditions such as hyperalgesia, which it does not fully explain. The relief of pain by electrical stimulation of a peripheral nerve, or even of the spinal cord, may be due to a frequency-related conduction block which acts on primary afferent branch points where dorsal column fibers and dorsal horn collaterals diverge. Spinal cord stimulation patients tend to show a preference for a minimum pulse repetition rate of 25 Hz.

Stimulation may also involve direct inhibition of an abnormally firing or damaged nerve. A damaged nerve may be sensitive to slight mechanical stimuli (motion) and/or noradrenaline (a chemical utilized by the sympathetic nervous system), which in turn results in abnormal firing of the nerve's pain fibers. It is theorized that stimulation relieves this pain by directly inhibiting the electrical firing occurring at the damaged nerve ends.

Stimulation is also thought to control pain by triggering the release of endorphins. Endorphins are considered to be the body's own pain-killing chemicals. By binding to opioid receptors in the brain, endorphins have a potent analgesic effect.

Recently, an alternative to 1) TENS, 2) percutaneous stimulation, and 3) bulky implantable stimulation assemblies has been introduced. Small, implantable microstimulators have been introduced that can be injected into soft tissues through a cannula or needle. The most specific of these, the bion, can produce electrical energy through a tiny battery that does not require wires or leads to be active. The negative with this therapy however is that the recharge capacity of these products is very poor, and that they do not have the capacity to deliver therapy for prolonged periods of time. In addition, like all other neurostimulators, these products are designed for continual stimulation therapy. There are a wide variety of indications that are not treated by current neurostimulation device methods which require therapy only on an as needed basis. The therapy is ongoing, however it isn't continual throughout the day. Providing therapy in this manner will allow for the introduction of a product that can be miniscule in size and be driven by limited power without sacrificing long term viability of the device itself.

Underlying Technology

The heart of the implanted power source is a high-sensitivity, passive magnetostrictive/electro-active magnetic field sensor, e.g. a Ferro Solution $g_{33}$ mode (PME-33) magnetic sensor depicted schematically in FIG. 12. Other magnetostrictive/electroactive devices, e.g. $g_{31}$ devices, could also work with this system. This magnetic field sensor converts magnetic field variations seen by the magnetic layer(s) to a magnetostrictive stress, σ, some of which is transmitted to the electro-active element to which it is bonded. The stressed electro- active element develops a voltage across its electrodes. The coupling coefficient $g_{33}$ can have values ranging from about 0.015 V/m-Pa for ceramic PZT, to 0.1 V/m-Pa for single-crystal electro-active materials. Typically, $g_{33}$ is 3 or 4 times greater than $g_{31}$ used in all other reported, prior-art PME sensors. Magnetostrictive stresses can be as large as 60 MPa [for Terfenol-D, $Fe_2$(Tb,Dy)]. Thus, the PME-33 sensors have a theoretical limiting magneto-electric sensitivity of order $6 \times 10^7$ V/(m-T), much greater than that of a similar $g_{31}$ device. In prototype PME-33 devices similar to that shown in FIGS. 12 and 13, linear response of 5 V/Oe has been measured and fields as small as 2 μT (20 mOe) have already been measured. It is possible to significantly enhance the sensitivity of this device by applying an AC bias to the magnetic layer(s).

A magneto-electric sensitivity or quality factor, $Q_{me}$ (V/T) can be defined for PME sensors.

We can estimate the limiting values for $Q_{me}$ using known material parameters. One material combination we have used, amorphous magnetic alloy and PVDF electro-active material. Other material combinations used in our PME devices include either Terfenol-D or Fe—Co magnetostrictive layers with PZT electroactive materials. These typically give devices that produce 10s of V/Oe. One could also use Fe—Ga magnetostrictive material with any of the electroactives including single-crystal or electrostrictive materials, indicates that for a 1 cm long sensor (L≈10−2 m), the theoretical output voltage per unit field is:

$$Q_{me}^{amorph-PVDF} \approx 2.1 \times 10^5 \text{ (V/T)} [Q_{me}^{amorph-PVDF}=21 \text{ (V/Oe)}] \quad (1)$$

The magnetic field that drives this sensor (and thus makes it function as a remote energy harvester and/or voltage generator) is provided by an external power source that is connected to a small, flat-profile coil antenna. Such an antenna generates a near field that is mainly magnetic in character.

Example of one Embodiment

Consider a 3 cm-diameter, ten-turn coil with each turn (made from wire or a flat foil or film) having a cross section of 0.05×1 mm; it would have a resistance of less than 1 Ohm. When driven by a 10 $V_{rms}$ AC signal (possibly battery-powered), it would draw a current of 20-30 A producing a field of order 100 Oe 1 or 2 cm beneath the coil. This is more than enough to produce a significant rotation in the magnetization of the PME sensor. The antenna will dissipate only a few Wafts while it is activated. The PME-33 sensor/harvester will generate several hundreds of Volts (depending on its size as well as the circuit and device it drives). The PME sensor is essentially a capacitor that has a value of C typically in the range of 0.1-10 nF. Thus the power stored on the capacitor under the action of a magnetic field alternating at the resonance frequency of the PME sensor, typically 10-30 kH for cm-scale devices) will be in the range of tens of Watts. The power that can be drawn from the PME-33, estimated to be hundreds of mW based on the efficiency of these devices, can be used immediately or stored in a small implanted battery.

The field generated normal to the pancake coil as a function of distance, b, from the coil along its normal is readily calculated. Here l is the current, A is the loop antenna area, $\pi a^2$, and b is the distance from the antenna in cm. FIG. 14 shows the decrease in field-strength in Oe-per-ampere with distance b along the axis of symmetry of a 3-cm-diameter coil. At a distance equal to the coil radius H is about ⅓$^{rd}$ of its value at b=0. In various applications, the coil, the AC circuit powering it, the configuration of the PME-33 receiver and its power-conditioning circuit can each be modified to optimally meet the implant power needs. For example, for pain relief by nerve stimulation, a very short pulse of high voltage at low current is needed. In this case, more current should be provided by the external power source and the coil should contain more turns of low-resistance wire to increase the field generated.

It should be noted that more power can be harvested by a PME sensor from the external field if the field is applied at the resonance frequency of the sensor. For $g_{33}$ devices that are symmetric about their mid-plane (no bending modes), the lowest frequency resonance is due to a longitudinal, standing acoustic wave between the electrodes. This mode occurs at a frequency close to $$f = \frac{1}{2\Lambda} \sqrt{\frac{E}{\rho}},$$

where L is the distance between the electrodes, E is the effective modulus of the device and p is the average mass density of the device. For PME sensors that we have made on the cm scale, the resonance frequency is a few t of kHz.

Method of Utilization and Delivery:

In one embodiment the PME or PME like device, either singular or multiple, would be placed adjacent to the therapeutic bed whether nerve, tissue, or solid organ. These pellets are charged with power transfer from an external coil. The pellets can assume varying charge either in a singular or plural form. Each PME can be an anode or a cathode (positive or negative) and each pellet can change its state by external signal from anode to cathode or vice versa. In addition the PME can function as a sensor, therefore the movement of electrical power between the PME pellets can be determined as a function of time. This can allow for selective delivery of electricity to involved muscle groups while sparing body areas not involved in therapy providing a greater degree of therapeutic benefit.

The disclosures of all of the following articles and publications is hereby incorporated by reference herein.

U.S. Patent application: "Novel, high sensitivity, passive magnetic field sensor", Jiankang Huang and Robert C. O'Handley, Filing date: provisional, Dec. 9, 2002, Formal, Dec. 8, 2003, Application Number: 60/431,487.

U.S. Pat. No 6,984,902 B1. Jan. 10, 2006, "Novel, high efficiency, vibration energy harvester", Jiankang Huang, Robert C. O'Handley, and D. Bono. Filing date: provisional, Feb. 3, 2003, Formal, Jan. 29, 2004. Application Number: 60/444,562.

"New, high-sensitivity, hybrid magnetostrictive/electroactive magnetic field sensors", Jingkang Huang, R. C. O'Handley and D. Bono, SPIE Conf. Proc., 5050, 229 (2003).

"Passive, solid-state magnetic field sensors and applications thereof" Yi Qun Li, r. C. O'Handley and G.Dionne, U.S. Pat. No. 6,279,406 B1, issued Aug. 28, 2001.

"High magnetoelectric properties in 0.68 Pb($Mg_{1/3\ Nb2/3}$)$O_3$0.32$PbTiO_3$ single cryatal and Terenol-D laminate composites", J. Ryu et al., J. Korean Ceramic Soc 39, 813, (2002).

"Magnetoelectric properties in piezoelectric and magnetostrictive laminate composites" J. Ryu et al, Jpn. J. Appl. Phys 40, 4948 (2001).

Multilayered, unipoled Piezoelectric Transformers", s. Priya et al, Jpn. J. Appl. Phys. 43, 3503 (2004).

"Enhanced magnetoelectric effects in aminate composites of Terfenol-D/Pb(Zr,Ti) $O_3$ under resonant drive", S. Dong et al. Appl. Phys. Lett. 83, 4812 (2003).

"Longitudinal and transverse magnetoelectric voltage coefficients of magnetostrictive/piezoelectric laminate composite: Theory", S. Dong et al. IEEE Trans. Ultrasonics, ferroelectrics and Freq. control 50, 1253 (2003).

"Magnetoelectric coupling in Terfenol-D/polyvinylidenedifluoride composites" K. Mori and M. Wuttig, J. Appl. Phys. 81, 100 (2002).

Although exemplary embodiments of the invention have been disclosed, it will be apparent to those skilled in the art that various changes and modifications can be made which will achieve all or some of the advantages of the invention.

The invention claimed is:

1. An energy harvester without a local field source comprising:
a magnetic field sensing element including one or more layers of magnetostrictive material having a magnetization vector that responds to variations in an applied magnetic field by generating a stress, and one or more layers of electroactive material, mechanically bonded to the layer of magnetostrictive material, that responds to the stress by generating a voltage; and
a circuit coupled to the sensing element that converts the voltage to electrical power for immediate use or storage, wherein the sensing element either:
a) moves relative to a remote static external magnetic field, such that changes in orientation of the sensing element with respect to the external field generates the voltage; or
b) is stationary with respect to a remote changing external magnetic field, wherein the changing external field causes the sensing element to generate the voltage.

2. The energy harvester of claim 1, wherein the electrical power comprises a voltage and current suitable for an intended application.

3. The energy harvester of claim 1, wherein the magnetostrictive material layer has a magnetization vector that responds to variations in the magnetic field by rotating in a plane and wherein the electroactive material is poled in a direction substantially parallel to the plane in which the magnetization vector rotates.

4. The energy harvester of claim 1, wherein the variations in the applied external field are in one or more of magnitude and direction of the field.

5. The energy harvester of claim 1, wherein the sensing element includes electrodes for measuring the voltage generated and wherein the electrodes are configured such that the distance between the electrodes and cross sectional area between the electrodes are tailored to produce a desired electrical power.

6. The energy harvester of claim 1, wherein the remote magnetic field is generated by one or more of an electrical transformer, motor, actuator, switch, electronic device, moving machinery or inductor.

7. The energy harvester of claim 6, wherein the inductor is a wire or coil through which an alternating current is flowing, to produce the remote changing external magnetic field.

8. The energy harvester of claim 1, wherein the changing external field or sensing element movement is at vibration or power transmission frequencies of no greater than 1 kHz.

9. The energy harvester of claim 1, wherein the changing external field is at a resonance frequency in the range of that of the sensing element.

10. The energy harvester of claim 9, wherein the changing external field is in a range of 20 to 50 kHz.

11. The energy harvester of claim 9, wherein the external field frequency is equal to or close to the resonance frequency of the sensor, which varies roughly according to the equation $$fr \approx \frac{1}{2L}\sqrt{\frac{E_{eff}}{\rho_{eff}}}$$

where L is a characteristic length of the sensor and $E_{eff}$ and $p_{eff}$ are the elastic modulus and mass density appropriate to describe the composite magnetostrictive/electroactive sensor properties.

12. The energy harvester of claim 1, wherein the changing external field and sensing element are within a resonant frequency range.

13. The energy harvester of claim 12, wherein the circuit is within the resonant frequency range.

14. The energy harvester of claim 9, wherein the external changing field is outside a human or other animal body and the sensing element is inside the body.

15. A method of harvesting energy comprising:
providing a magnetic field sensing element including one or more layers of magnetostrictive material having a magnetization vector that responds to variations in an applied magnetic field by generating a stress, and one or more layers of an electroactive material, mechanically bonded to the layer of magnetostrictive material, that responds to the stress by generating a voltage;
wherein the voltage is generated by either:
moving the sensing element relative to a remote static external magnetic field, such that changes in orientation in the sensing element with respect to the external field generates the voltage; or
the sensing element is stationary with respect to a remote changing external magnetic field, and the changing external field causes the sensing elemenet to generate the voltage; and
converting the generated voltage to electrical power for immediate use or storage.

* * * * *

UNITED STATES PATENT AND TRADEMARK OFFICE
CERTIFICATE OF CORRECTION

| | | |
|---|---|---|
| PATENT NO. | : 7,952,349 B2 | Page 1 of 1 |
| APPLICATION NO. | : 11/734181 | |
| DATED | : May 31, 2011 | |
| INVENTOR(S) | : Huang et al. | |

It is certified that error appears in the above-identified patent and that said Letters Patent is hereby corrected as shown below:

In the Abstract, line 5, "of" (first occurrence) should be -- or --.

In column 20, line 34, "$p_{eff}$" should be -- $\rho_{eff}$ --.

In column 20, line 60, "elemenet" should be -- element --.

Signed and Sealed this
Sixteenth Day of August, 2011

David J. Kappos
*Director of the United States Patent and Trademark Office*